United States Patent
Cooke

(10) Patent No.: US 11,266,653 B2
(45) Date of Patent: Mar. 8, 2022

(54) COMBINATION THERAPY

(71) Applicant: Novartis AG, Basel (CH)

(72) Inventor: Vesselina Cooke, Newton, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/610,482

(22) PCT Filed: Apr. 30, 2018

(86) PCT No.: PCT/IB2018/052989
§ 371 (c)(1),
(2) Date: Nov. 1, 2019

(87) PCT Pub. No.: WO2018/203219
PCT Pub. Date: Nov. 8, 2018

(65) Prior Publication Data
US 2020/0246346 A1 Aug. 6, 2020

Related U.S. Application Data

(60) Provisional application No. 62/500,108, filed on May 2, 2017, provisional application No. 62/656,423, filed on Apr. 12, 2018.

(51) Int. Cl.
*A61K 31/5377* (2006.01)
*A61K 31/519* (2006.01)
*A61P 35/00* (2006.01)

(52) U.S. Cl.
CPC ........ *A61K 31/5377* (2013.01); *A61K 31/519* (2013.01); *A61P 35/00* (2018.01)

(58) Field of Classification Search
CPC .... A61K 2300/00; A61K 31/18; A61K 31/44; A61K 31/4523; A61K 31/519; A61K 31/5377; A61K 45/06; A61P 35/00
See application file for complete search history.

(56) References Cited

U.S. PATENT DOCUMENTS

| | | |
|---|---|---|
| 2014/0275003 A1 | 9/2014 | Barsanti et al. |
| 2015/0216868 A1 | 8/2015 | Laquerre et al. |
| 2016/0038504 A1 | 2/2016 | Aversa et al. |
| 2017/0202842 A1 | 7/2017 | Laquerre et al. |
| 2017/0260207 A1 | 9/2017 | Aversa et al. |

FOREIGN PATENT DOCUMENTS

| | | | | |
|---|---|---|---|---|
| WO | 2014039375 A1 | 3/2014 | | |
| WO | WO 2014/039375 | * 3/2014 | ........... | A61K 31/519 |
| WO | 2014151616 A1 | 9/2014 | | |
| WO | WO 2014//151616 | * 9/2014 | ........... | C07D 403/12 |
| WO | 2018051306 A1 | 3/2018 | | |

OTHER PUBLICATIONS

Whittaker, et al., "Combined Pan-RAF and MEK Inhibition Overcomes Multiple Resistance Mechanisms to Selective RAF Inhibitors", Molecular Cancer Therapeutics, 14(12):2700-2711. 2015.
Lito et al., "Disruption of CRAF-Mediated MEK Activation Is Required for Effective MEK Inhibition in KRAS Mutant Tumors", Cancer Cell, 25(5):697-710. 2014.
Atefi et al., "Combination of pan-RAF and MEK inhibitors in NRAS mutant melanoma," Molecular Cancer, vol. 14, No. 27, pp. 1-12, 2015.

* cited by examiner

*Primary Examiner* — Erich A Leeser
(74) *Attorney, Agent, or Firm* — Scott W. Reid

(57) ABSTRACT

The present invention relates to a pharmaceutical combination comprising (a) a Raf inhibitor as defined herein, or a pharmaceutically acceptable salt thereof and (b) a MEK inhibitor, particularly trametinib, particularly for use in the treatment of a proliferative disease. This invention also relates to uses of such combination for preparation of a medicament for the treatment of a proliferative disease; methods of treating a proliferative disease in a subject in need thereof comprising administering to said subject a jointly therapeutically effective amount of said combination; use of such combination for the treatment of proliferative disease; pharmaceutical compositions comprising such combination and commercial packages thereto.

13 Claims, 21 Drawing Sheets

Dabrafenib

|  | BRAF$^{mut}$ | KRAS$^{mut}$ | NRAS$^{mut}$ | WT |
|---|---|---|---|---|
| Sensitive (#) | 28 | 1 | 4 | 11 |
| Resistant (#) | 19 | 85 | 29 | 180 |
| Fisher's Exact Test p-value vs. WT | 1.9E-15 | 0.11 | 0.25 | 1 |

Compound (II)

|  | BRAF$^{mut}$ | KRAS$^{mut}$ | NRAS$^{mut}$ | WT |
|---|---|---|---|---|
| Sensitive (#) | 30 | 19 | 13 | 11 |
| Resistant (#) | 17 | 67 | 20 | 180 |
| Fisher's Exact Test p-value vs. WT | 3.09E-17 | 1.19E-04 | 1.26E-06 | 1 |

NSCLC Primary Tumor Xenograft (PTX) Models

COMBINATION THERAPY

RELATED APPLICATIONS

This application is a U.S. National Phase filing of International Application Ser. No. PCT/IB2018/052989 filed 30 Apr. 2018 and claims priority to U.S. Provisional Application Ser. No. 62/500,108 filed 2 May 2017 all of which are incorporated in their entireties herein.

FIELD OF THE INVENTION

This invention relates to a pharmaceutical combination comprising (a) a Raf inhibitor selected from the group consisting of Compound of formula (I), as defined herein, or a pharmaceutically acceptable salt thereof, or Compound of formula (II), as defined herein, or a pharmaceutically acceptable salt thereof, and (b) a MEK inhibitor, particularly trametinib, or a pharmaceutically acceptable salt or solvate thereof. This invention also relates to a pharmaceutical combination comprising (a) a Raf inhibitor selected from the group consisting of Compound of formula (I), as defined herein, or a pharmaceutically acceptable salt thereof, or Compound of formula (II), as defined herein, or a pharmaceutically acceptable salt thereof, and trametinib, or a pharmaceutically acceptable salt or solvate thereof.

This invention also relates to such combinations for use in the treatment of a proliferative disease, in particular a cancer, uses of such combinations for the preparation of a medicament for the treatment of a proliferative disease, in particular a cancer; methods of treating a proliferative disease, in particular a cancer, in a subject in need thereof comprising administering to said subject a jointly therapeutically effective amount of said combinations; use of such combinations for the treatment of a proliferative disease, in particular a cancer; pharmaceutical compositions comprising such combinations and commercial packages thereto.

This invention also relates to Compound of formula (I), as defined herein, or a pharmaceutically acceptable salt thereof, or Compound of formula (II), as defined herein, or a pharmaceutically acceptable salt thereof, for use in a combination therapy with a MEK inhibitor, particularly trametinib, or a pharmaceutically acceptable salt or solvate thereof. There is also provided herein a MEK inhibitor, particularly trametinib, or a pharmaceutically acceptable salt or solvate thereof, for use in a combination therapy with Compound of formula (I), as defined herein, or a pharmaceutically acceptable salt thereof, or for use in a combination therapy with Compound of formula (II), as defined herein, or a pharmaceutically acceptable salt thereof.

BACKGROUND

The RAS/RAF/MEK/ERK or MAPK pathway is a key signaling cascade that drives cell proliferation, differentiation, and survival. Dysregulation of this pathway underlies many instances of tumorigenesis. This pathway is activated by extracellular signals that in turn induces the small G protein RAS to exchange GDP for GTP. The activated RAS small guanidine triphosphatase (GTPase) promotes the activation of the RAF (also referred to as "Raf" herein) family proteins (ARAF, BRAF and CRAF, also known as RAF1). Activated RAF proteins lead to the phosphorylation and activation of MEK1/2 proteins, which subsequently phosphorylate and activate extracellular signal-regulated kinases (ERKs). ERK1/2 proteins phosphorylate a variety of substrates, including multiple transcription factors, and regulate key cellular activities, including proliferation, differentiation, migration, survival and angiogenesis.

Aberrant signaling or inappropriate activation of the MAPK pathway has been shown in multiple tumor types, including melanoma, lung and pancreatic cancer, and can occur through several distinct mechanisms, including activating mutations in RAS and BRAF (V-Raf Murine Sarcoma Viral Oncogene Homolog B1). RAS which is a superfamily of GTPases includes KRAS (v-Ki-ras2 Kirsten rat sarcoma viral oncogene homolog), which is a regulated signaling protein that can be turned on (activated) by various single-point mutations, which are known as gain-of-function mutations. RAS mutations, particularly gain-of-function (GOF) mutations, have been detected in 9-30% of all cancers, with KRAS mutations having the highest prevalence (86%), followed by NRAS (11%), and, infrequently, HRAS (3%) (Cox AD, et al, *Nat Rev Drug Discov* 2014;13(11):828-51). Activating KRAS mutations are also frequently found in melanoma (Fedorenko IV, et al, *Br J Cancer* 2015;112(2): 217-26), pancreatic cancer (di Magliano MP & Logsdon CD, *Gastroenterology* 2013;144(6):1220-9), colorectal cancer (Knickelbein K & Zhang L, *Genes Dis* 2015;2(1):4-12) and ovarian cancer (Nakayama N, et al, *Br J Cancer* 2008;99 (12):2020-8).

Inhibitors that target downstream effectors of RAS, such as RAF, MEK, and ERK kinases, have not demonstrated significant clinical activtiy in RAS-driven tumors. For example, RAF inhibitors, such as vemurafenib which are efficacious in BRAF $v^{600}$-mutant melanomas, are ineffective in RAS mutant cancers. There are thus currently no effective therapies for KRAS-mutant tumors and NRAS-mutant tumors. In particular, unlike BRAF mutant melanoma, there are no approved targeted therapies for NRAS mutant melanoma patients. Recent data from a trial of a MEK1/2 inhibitor demonstrated a small increase in progression free survival but no improvement in overall survival in these patients (Dummer et al., *Lancet Oncol*, 18, 435-445, 2017).

Although some vertical combinations of MAPK inhibitors have proved beneficial, it is not always predictable whether any one of the various permutations of possible combinations would be of clinical benefit. For example, it was recently reported that a combination of the MEK inhibitor cobimetinib in combination with the ERK1/2 inhibitor GDC-0994 led to overlapping and cumulative toxicity, which, according to the authors, would restrict further development of this particular combination. (Weekes et al 2017, Abstract CT107:AACR Annual Meeting 2017; Apr. 1-5, 2017 Combinations)

Lung cancer is a common type of cancer that affects men and women around the globe. NSCLC is the most common type (roughly 85%) of lung cancer with approximately 70% of these patients presenting with advanced disease (Stage IIIB or Stage IV) at the time of diagnosis. About 30% of NSCLC tumors contain activating KRAS mutations, and these mutations are associated with resistance to epidermal growth factor receptor tyrosine kinase inhibitors (EGFR TKIs) (Pao W, et al, *PLoS Med* 2005;2(1):e17). To date, no approved targeted therapies are available for patients suffering from NSCLC with KRAS mutation and from NSCLC with BRAF mutations other than V600E.

Melanoma is a common type of cancer that affects men and women around the globe. 50% of metastatic cutaneous melanoma patients harbor a BRAF-activating mutation and 20% of these patients harbour an NRAS-activating mutation (Zhang et al, *Pigment Cell Melanoma Res* 2016; 29:266-283. NRAS mutations were identified as an independent predictor of shorter survival after a diagnosis of stage IV melanoma (Jakob JA et al (2012), Cancer, Volume 118, Issue 16, Pages 4014-4023).

Direct inhibition of KRAS and NRAS is thus still proving challenging and to date no approved targeted therapies are available for patients with KRAS-mutant cancers, such as KRAS mutant NSCLC, and NRAS-mutant cancers, such as NRAS mutant melanoma. Thus, there is a need for targeted therapy that is safe, is well tolerated, and/or is accompanied with fewer adverse side-effects such as skin rash. A therapy which results in durable and sustained responses in a clinical setting is also needed.

SUMMARY

It has now been found that that a combination of a MEK inhitbitor and a selective Raf inhibitor, such as the Compound of formula (I) as defined herein, that potently inhibit the activity of both CRAF and BRAF may be effective in blocking BRAF-mutant tumors and RAS-mutant driven tumorigenesis. Combining Compound of formula (I) and trametinib was found to be synergistic in MAPK-mutant cancer cell lines such NRAS-mutant and KRAS-mutant cell lines cell lines. Based on the findings described herein, a combination of a Raf inhibitor, particularly a CRAF- and BRAF-inhibitor such as a Compound of formula (I), with a MEK inhibitor, such as trametinib, may be particularly efficacious and less susceptible to resistance in patients suffering from RAS-mutant tumors.

The combination of Compound of formula (I) with trametinib also demonstrated increased anti-tumor response compared to either single-agent therapy in human KRAS mutant NSCLC, CRC, and PDAC xenograft models, and human NRAS mutant melanoma xenograft models. The combination of Compound of formula (II) with trametinib demonstrated increased efficacy of tumor response compared to either single-agent therapy in a human HPAFII pancreatic xenograft mouse model. Therefore, Compound of formula (I) or Compound of formula (II), alone and in combination with a MEK inhibitor, may be useful in the treatment of patients with cancers harboring MAPK pathway alterations. Such cancers include KRAS-mutant NSCLC (non-small cell lung cancer), KRAS-mutant pancreatic cancer (e.g. KRAS-mutant pancreatic ductal adenocarcinoma (PDAC), KRAS-mutant CRC (colorectal cancer), and NRAS-mutant melanoma).

The present invention thus provides a pharmaceutical combination comprising (a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, and (b) a MEK inhibitor, particularly trametinib, or a pharmaceutically acceptable salt or solvate thereof The present invention also provides such a combination for use in the treatment of a proliferative disease.

In addition, the present invention provides:
(a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, for use in a combination therapy with a MEK inhibitor, particularly trametinib, or a pharmaceutically acceptable salt or solvate thereof; and
(b) a MEK inhibitor, particularly trametinib, or a pharmaceutically acceptable salt or solvate thereof, for use in a combination therapy with a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof.

Compound of formula (I) is the compound with the following structure:

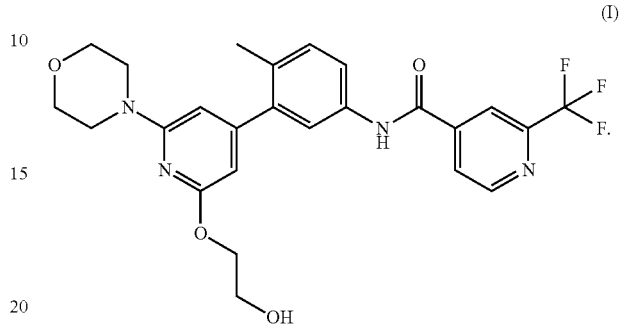

(I)

Compound of formula (II) is the compound with the following structure:

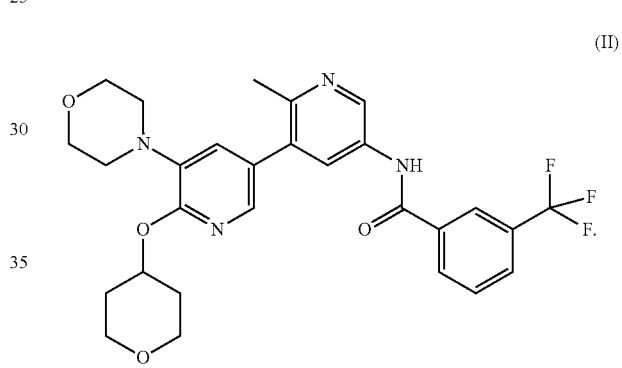

(II)

The present invention further provides a pharmaceutical combination comprising a Raf inhibitor compound, as defined herein, or a pharmaceutically acceptable salt thereof, and a MEK inhibitor, preferably trametinib, or a pharmaceutically acceptable salt or solvent thereof, particularly for simultaneous, separate or sequential use in the treatment of a proliferative disease.

In another preferred embodiment, the pharmaceutical combination of the present invention comprises (a) a Raf inhibitor Compound of formula (I), or a pharmaceutically acceptable salt thereof, and (b) trametinib, or a pharmaceutically acceptable salt or solvate thereof, in particular a solvate thereof.

In another preferred embodiment, the pharmaceutical combination of the present invention comprises (a) a Raf inhibitor Compound of formula (II), or a pharmaceutically acceptable salt thereof, and (b) trametinib, or a pharmaceutically acceptable salt or solvate thereof, in particular a solvate thereof.

The present invention is particularly related to the combination of the invention for use in the treatment of a cancer characterized by activating mutations in the MAPK pathway, and in particular by one or more mutations in RAS (e.g. KRAS or NRAS) and/or BRAF.

The present invention also provides the use of the combination of the invention for the treatment of a proliferative disease, particularly a cancer. In particular, the combination of the invention may be useful for the treatment of non-small cell lung cancer (NSCLC), melanoma, pancreatic ductal adenocarcinoma (PDAC), cervical cancer, ovarian cancer or colorectal cancer (CRC).

The present invention also provides the use of the combination of the invention for the preparation of a medicament for the treatment of a proliferative disease, particularly a cancer.

The present invention also provides a method of treating a proliferative disease comprising simultaneously, separately or sequentially administering to a subject in need thereof a combination of the invention in a quantity which is jointly therapeutically effective against said proliferative disease.

The present invention also provides a pharmaceutical composition or combined preparation comprising a quantity of the combination of the invention, which is jointly therapeutically effective against a proliferative disease, and optionally at least one pharmaceutically acceptable carrier.

The present invention also provides a combined preparation comprising (a) one or more dosage units of a Raf inhibitor selected from the group consisting of (i) Compound of formula (I), or a pharmaceutically acceptable salt thereof, and (ii) Compound of formula (II), or a pharmaceutically acceptable salt thereof, and (b) one or more dosage units of a MEK inhibitor, preferably trametinib, or a pharmaceutically acceptable salt or solvate thereof, for use in the treatment of a proliferative disease.

The present invention also provides a commercial package comprising as active ingredients a combination of the invention and instructions for simultaneous, separate or sequential administration of a combination of the invention to a patient in need thereof for use in the treatment of a proliferative disease, preferably non-small cell lung cancer (NSCLC), melanoma, pancreatic ductal adenocarcinoma (PDAC), cervical cancer, ovarian cancer or colorectal cancer (CRC).

The present invention also provides a commercial package comprising a Raf inhibitor selected from the group consisting of (i) Compound of formula (I), or a pharmaceutically acceptable salt thereof, and (ii) Compound of formula (ii), or a pharmaceutically acceptable salt thereof, and instructions for the simultaneous, separate or sequential use with a MEK inhibitor, preferably trametinib, or a pharmaceutically acceptable salt or solvate thereof, in the treatment of a proliferative disease.

Various aspects of the invention are described in further detail below. Additional definitions are set out throughout the specification.

DUSP6 levels are represented as the percentage change in comparison to the vehicle group after normalization to control gene RPLPO.

Figure 15:
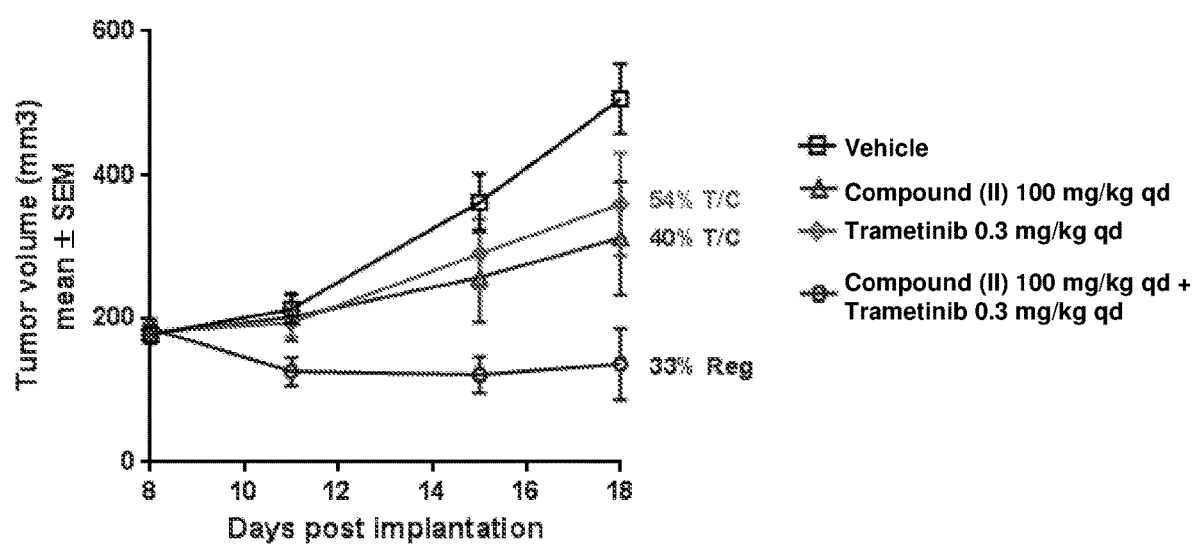

FIG. 15. In vivo activity of Compound of formula (II) and trametinib as single agents or in combination in the HPAF-II xenograft model. In vivo tumor growth following ten days of treatment as indicated. Compound was administered daily (qd). Anti-tumor activity was determined by assessing percentage of tumor volume in the treatment groups versus that in vehicle-treated (% T/C) or percentage of tumor regression compared to the starting volume (% regression, indicated as "% Reg" in FIG. 15).

Figure 16:
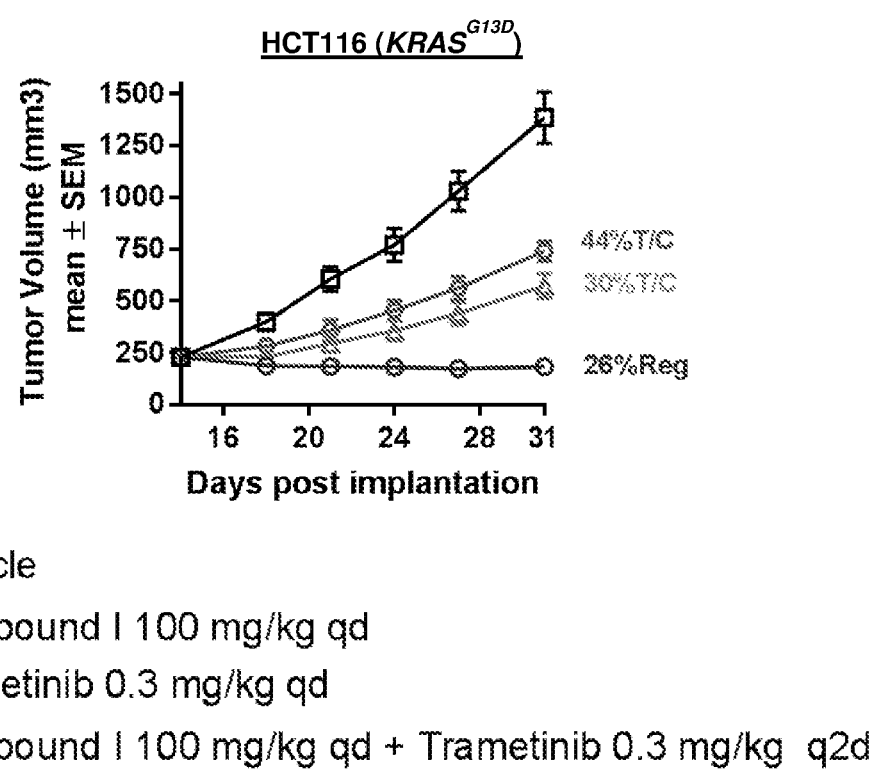

FIG. 16. A. In vivo activity of Compound of formula (I) (Compound I in Figure) and trametinib as single agents or in combination in HCT116 xenograft model. In vivo tumor growth following seventeen days of treatment as indicated. Compounds were administered daily (qd) or every other day (q2d). Anti-tumor activity was determined by assessing percentage of tumor volume in the treatment groups versus that in vehicle-treated (% T/C) or percentage of tumor regression compared to the starting volume (% regression, indicated as "% Reg" in FIG. 16).

Figure 17:
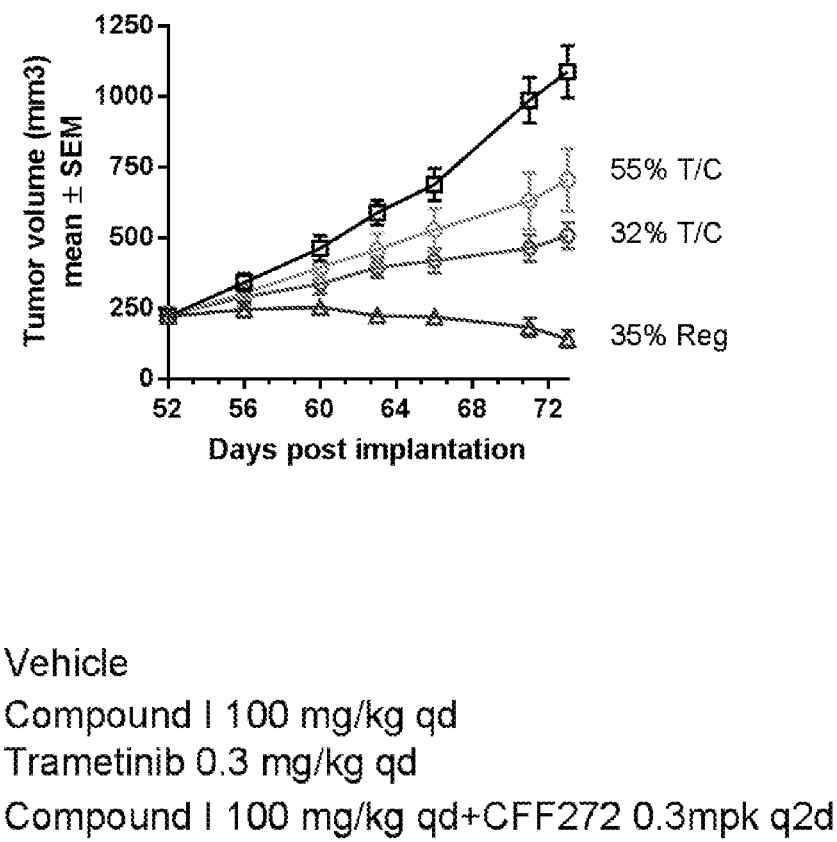

FIG. 17. A. In vivo activity of Compound of formula (I) (Compound I in Figure) and trametinib as single agents or in combination in 2043 xenograft model. In vivo tumor growth following 21 days of treatment as indicated. Compounds were administered daily (qd) or every other day (q2d). Anti-tumor activity was determined by assessing percentage of tumor volume in the treatment groups versus that in vehicle-treated (% T/C) or percentage of tumor regression compared to the starting volume (% regression, indicated as "% Reg" in FIG. 17).

Figure 18:
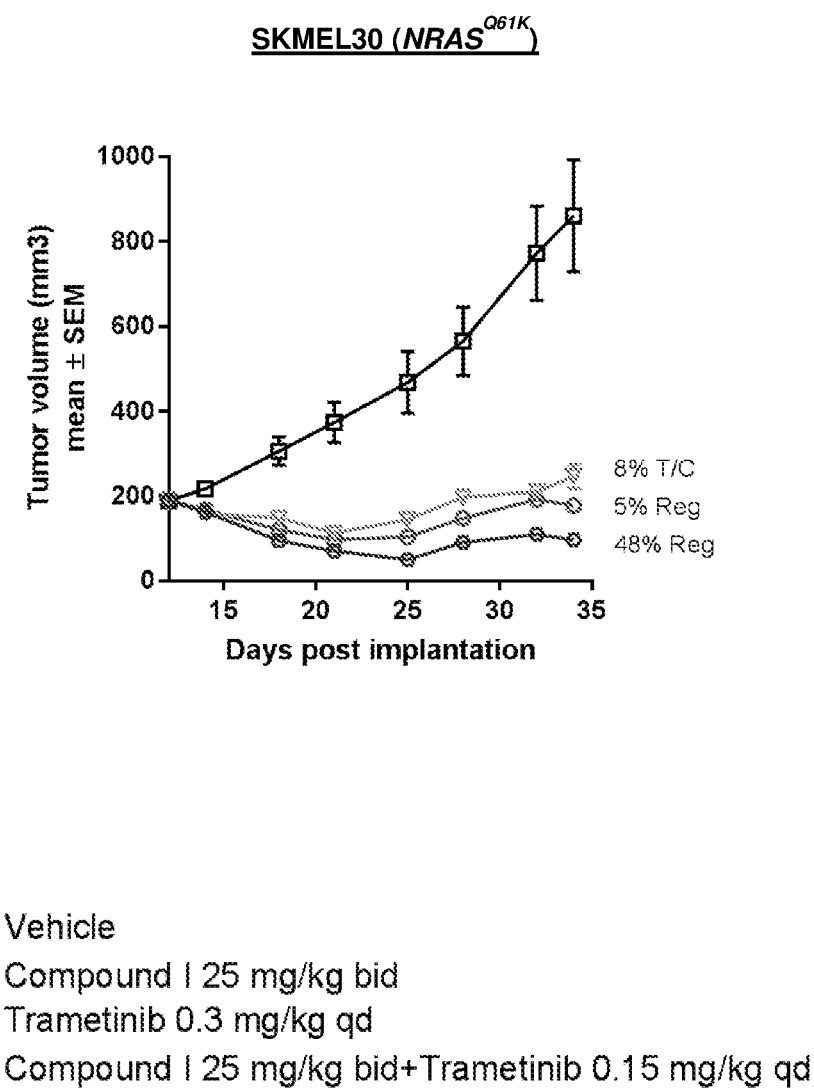

FIG. 18. A. In vivo activity of Compound of formula (I) (Compound I in Figure) and trametinib as single agents or in combination in SKMEL30 xenograft model. In vivo tumor growth following 22 days of treatment as indicated. Compounds were administered daily (qd) or twice daily (bid). Anti-tumor activity was determined by assessing percentage of tumor volume in the treatment groups versus that in vehicle-treated (% T/C) or percentage of tumor regression compared to the starting volume (% regression, indicated as "% Reg" in FIG. 18).

Figure 19:
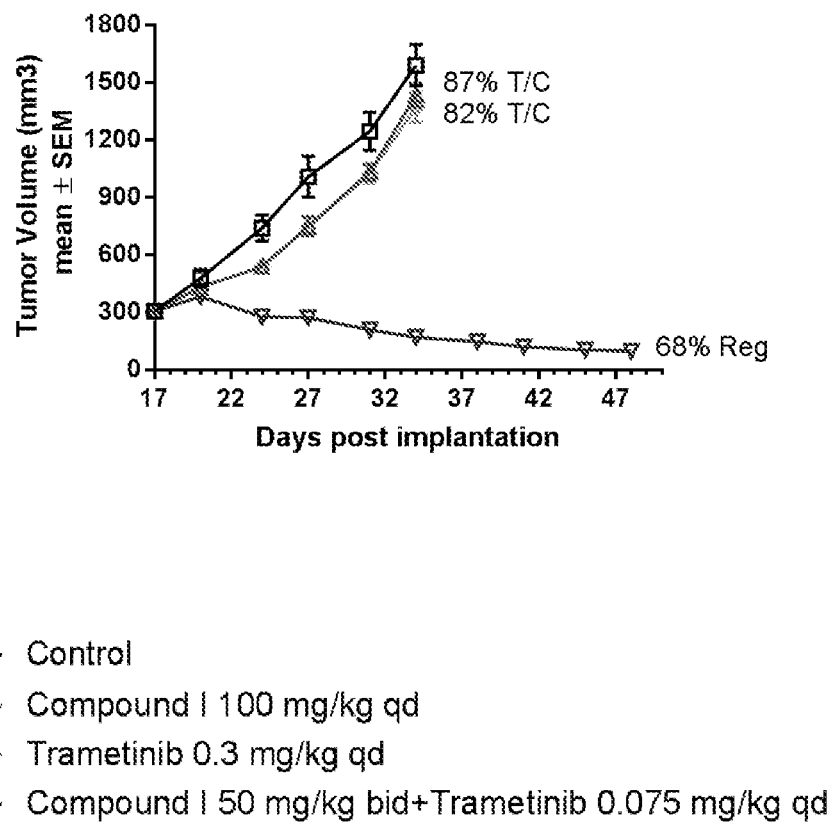

FIG. 19. A. In vivo activity of Compound of formula (I) (Compound I in Figure) and trametinib as single agents or in combination in 20667 xenograft model. In vivo tumor growth following 17 days of treatment (single agents) and 31 days of combination treatment as indicated. Compounds were administered daily (qd) or twice daily (bid). Anti-tumor activity was determined by assessing percentage of tumor volume in the treatment groups versus that in vehicle-treated (% T/C) on day 34 for single agents or percentage of tumor regression compared to the starting volume (% regression, indicated as "% Reg" in FIG. 19) on day 48 for the combination.

Figure 20:
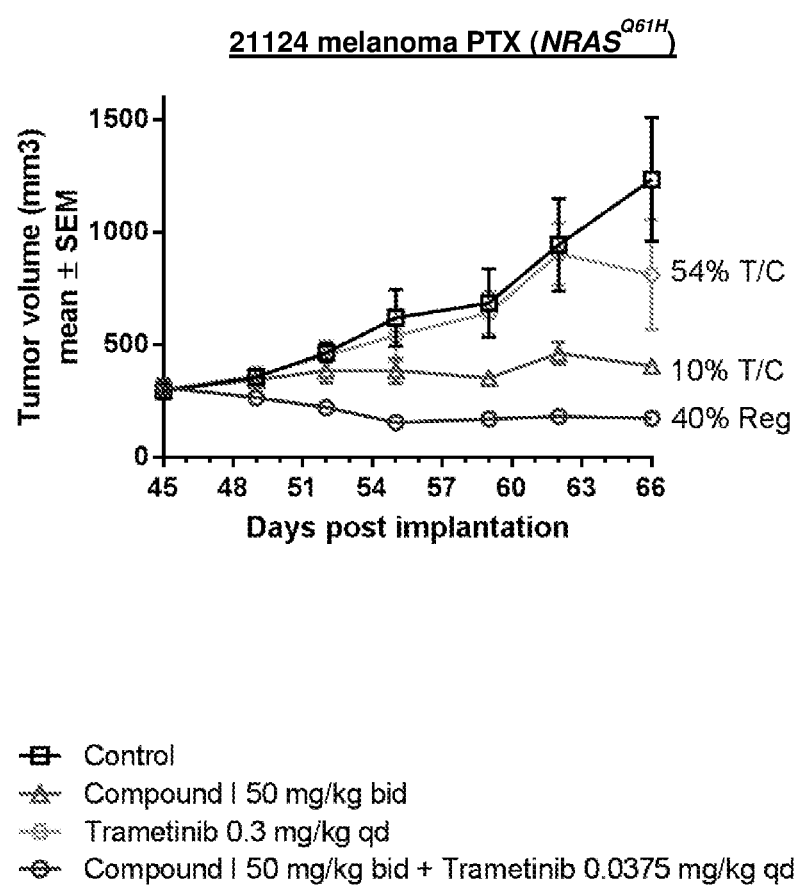

FIG. 20. A. In vivo activity of Compound of formula (I) (Compound I in Figure) and trametinib as single agents or in combination in 21124 xenograft model. In vivo tumor growth following 21 days of treatment as indicated. Compounds were administered daily (qd) or twice daily (bid). Anti-tumor activity was determined by assessing percentage of tumor volume in the treatment groups versus that in vehicle-treated (% T/C) or percentage of tumor regression compared to the starting volume (% regression, indicated as "% Reg" in FIG. 20).

Figure 21:
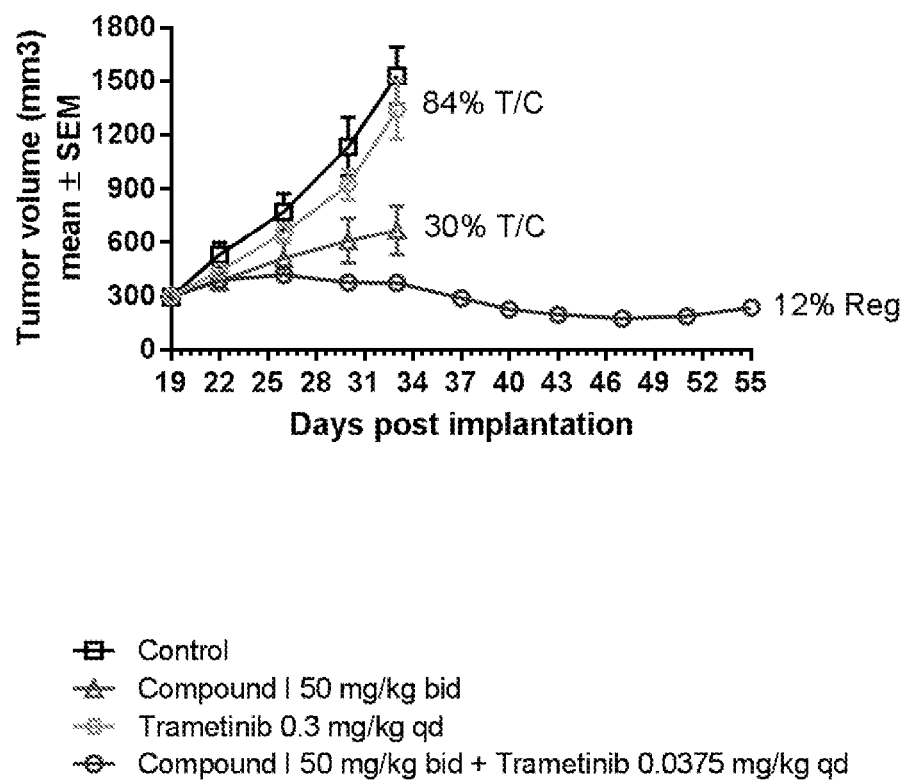

FIG. 21. A. In vivo activity of Compound of formula (I) (Compound I in Figure) and trametinib as single agents or in combination in 20864 xenograft model. In vivo tumor growth following 14 days of treatment (single agents) and 36 days of combination treatment as indicated. Compounds were administered daily (qd) or twice daily (bid). Anti-tumor activity was determined by assessing percentage of tumor volume in the treatment groups versus that in vehicle-treated (% T/C) on day 33 for single agents or percentage of tumor regression compared to the starting volume (% regression, indicated as "% Reg" in FIG. 21) on day 55 for the combination.

DETAILED DESCRIPTION OF THE INVENTION

The present invention relates to a pharmaceutical combination comprising (a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, and (b) a MEK inhibitor, particularly for use in the treatment of a proliferative disease.

As used herein, the term "Raf inhibitor" refers to an adenosine triphosphate (ATP)-competitive inhibitor of B-Raf protein kinase (also referred to herein as b-RAF, BRAF or b-Raf) and C-Raf protein kinase (also referred to herein as c-RAF, CRAF or c-Raf) that selectively targets, decreases, or inhibits at least one activity of serine/threonine-protein kinase B-Raf or C-Raf. The Raf inhibitor preferentially inhibits both Raf monomers and Raf dimers.

As used herein, the Raf inhibitor is selected from the group consisting of (i) Compound of formula (I), as defined herein, or a pharmaceutically acceptable salt thereof, and (ii) Compound of formula (II), as defined herein, or a pharmaceutically acceptable salt thereof.

Compound of formula (I) has the following structure:

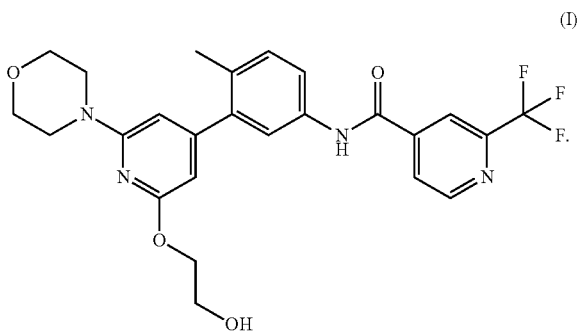 [SMILES: Cc1ccc(NC(=O)c2ccnc(C(F)(F)F)c2)cc1-c1cc(OCCO)nc(N2CCOCC2)c1]

(I)

For convenience, the group of the compound and its salts is collectively referred to as "Compound of formula (I)" or "Compound (I)", meaning that reference to "Compound of formula (I)" or "Compound (I)" will refer to any of the compound or pharmaceutically acceptable salt thereof in the alternative.

Raf inhibitor Compound of formula (I) and its pharmaceutically acceptable salts are described in WO2014/151616, which is hereby incorporated by reference in its entirety, and methods of its preparation have been described, for example, in Example 1156 therein.

Compound of formula (II) has the following structure:

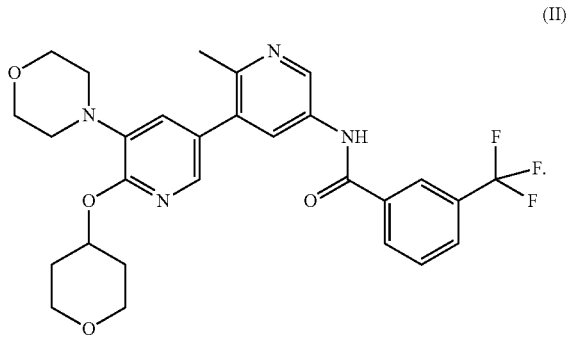 [SMILES: Cc1ncc(NC(=O)c2cccc(C(F)(F)F)c2)cc1-c1cnc(OC2CCOCC2)c(N2CCOCC2)c1]

(II)

For convenience, the group of the compound and its salts is collectively referred to as "Compound of formula (II)" or "Compound (II)", meaning that reference to "Compound of formula (II)" or "Compound (II)" will refer to any of the compound or pharmaceutically acceptable salt thereof in the alternative.

Raf inhibitor Compound of formula (II) and its pharmaceutically acceptable salts are described in WO2014/151616, which is hereby incorporated by reference in its entirety, and methods of its preparation have been described, for example, in Example 131 therein.

In cell-based assays, Raf inhibitors Compound of formula (I) and Compound of formula (II) demonstrated anti-proliferative activity in cell lines that contain a variety of mutations that activate MAPK signaling. In vivo, treatment with Compound of formula (I) or Compound of formula (II) generated tumor regression in several KRAS-mutant models including the NSCLC-derived Calu-6 (KRAS Q61K) and NCI-H358 (KRAS G12C). Collectively, in vitro and in vivo MAPK-pathway suppression and anti-proliferative activity observed for Compound of formula (I) or Compound of formula (II) at well-tolerated doses suggest that Compound of formula (I) or Compound of formula (II) may have anti-tumor activity in patients with tumors harboring activating lesions in the MAPK pathway. Moreover, Compound of formula (I) and Compound of formula (II) are a Type 2 ATP-competitive inhibitor of both B-Raf and C-Raf that keeps the kinase pocket in an inactive conformation, thereby reducing the paradoxical activation seen with many B-Raf inhibitors, and blocking mutant Ras-driven signaling and cell proliferation. Compound of formula (I) and Compound of formula (II) exhibited efficacy in numerous MAPK-driven human cancer cell lines and in xenograft tumors representing model tumors harboring human lesions in KRAS, NRAS and BRAF oncogenes.

Pharmaceutical combinations of the present invention further comprise a MEK inhibitor. The term "MEK inhibitor" is defined herein to refer to a compound which targets, decreases or inhibits at least one activity of MAP/ERK kinases 1 and 2 (MEK1/2).

Suitable MEK inhibitors for use in the combination of the present invention include, but are not limited to
a) trametinib (N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide), also referred to as JPT-74057 or GSK1120212, or a pharmaceutically acceptable salt or solvate thereof trametinib is disclosed in Example 4-1 in PCT Publication No. WO 2005/121142, which is hereby incorporated by reference in its entirety. As a monotherapy trametinib has been approved for the treatment of unresectable or metastatic malignant melanoma with B-Raf V600E or V600K mutations and the compound is commercially available from Novartis AG under the trade name Mekinist®.
b) PD0325901 (Pfizer) (disclosed in PCT Publication No. WO02/06213); PD184352 (Pfizer); Refametinib (also referred to as RDEA119 or Bay 86-9766); Cobimetinib, also referred to as XL518, and commercially available from Roche under the trade name Cotellic®; AS-701255 (Merck Serono); AS-701173 (Merck Serono); Pimasertib, also referred to as AS-703026 or MSC1936369B (Merck Serono); RDEA436 (Ardea Biosciences); RO4987655, also referred to as RG 7167 (Roche) and/or RG7420, also referred to as GDC-0623 (Roche), or a pharmaceutically acceptable salt thereof.

Preferably, the MEK inhibitor is trametinib, or a pharmaceutically acceptable salt or solvate thereof In some preferred embodiments, trametinib is in the form of a dimethyl sulfoxide solvate. In some embodiments, trametinib is in the form of a sodium salt. Suitably, trametinib is in the form of a solvate selected from: hydrate, acetic acid, ethanol, nitromethane, chlorobenzene, 1-pentancol, isopropyl alcohol, ethylene glycol and 3-methyl-1-butanol. These solvates and salt forms can be prepared by one of skill in the art from the description in WO 2005/121142.

The present invention further relates to a pharmaceutical combination comprising (a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof and (b) a MEK inhibitor, particularly for simultaneous, separate or sequential use in the treatment of a proliferative disease.

Selected terms are defined below and throughout the application. Compounds of the present invention are described using standard nomenclature. Unless defined otherwise, all technical and scientific terms used herein have the same meaning as is commonly understood by one of skill in the art to which this invention belongs. The following general definitions shall apply in this specification, unless otherwise specified:

As used herein the term "combination of the invention" refers to the combined administration comprised of (a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, and (b) a MEK inhibitor, preferably trametinib, or a pharmaceutically acceptable salt or solvate thereof. The Raf inhibitor Compound of formula (I), or a pharmaceutically acceptable salt thereof, and the MEK inhibitor, preferably trametinib, or a pharmaceutically acceptable salt or solvate thereof, or the Raf inhibitor Compound of formula (II), or a pharmaceutically acceptable salt thereof, and the MEK inhibitor, preferably trametinib, or a pharmaceutically acceptable salt or solvate thereof, may be employed in combination in accordance with the invention by administration simultaneously in a unitary pharmaceutical composition including both compounds. Alternatively, the combination may be administered separately in separate pharmaceutical compositions, each including one of the Raf inhibitors and a MEK inhibitor in a sequential manner wherein, for example, the Raf inhibitor or a MEK inhibitor is administered first and the other second. Such sequential administration may be close in time (e.g., simultaneously) or remote in time.

As used herein, the terms "a" and "an" and "the" and similar references in the context of describing the invention are to be construed to cover both the singular and the plural, unless otherwise indicated herein or clearly contradicted by context. Where the plural form is used for compounds, salts, and the like, this is taken to mean also a single compound, salt, or the like.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values. When describing a dosage herein as "about" a specified amount, the actual dosage can vary by up to 10% from the stated amount: this usage of "about" recognizes that the precise amount in a given dosage form may differ slightly from an intended amount for various reasons without materially affecting the in vivo effect of the administered compound.

When describing a dosage herein as a specified amount, i.e. without the term "about", the actual dosage can vary by up to 10% (preferably by up to 5%) from the stated amount: this usage recognizes that the precise amount in a given dosage form may differ slightly from an intended amount for various reasons without materially affecting the in vivo effect of the administered compound.

The terms "comprising" and "including" are used herein in their open-ended and non-limiting sense unless otherwise noted.

By "a combination" or "in combination with" it is not intended to imply that the therapy or the therapeutic agents must be physically mixed or administered at the same time and/or formulated for delivery together, although these methods of delivery are within the scope described herein. A therapeutic agent in these combinations can be administered concurrently with, prior to, or subsequent to, one or more other additional therapies or therapeutic agents. The therapeutic agents can be administered in any order. In general, each agent will be administered at a dose and/or on a time schedule determined for that agent. It will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized as single-agent therapeutics.

The combinations of the invention have therapeutic or protective functions or both. For example, these molecules may be administered to a human subject, to treat and/or prevent a variety of disorders, such as cancers as described herein.

The terms "combination", "therapeutic combination" or "pharmaceutical combination" as used herein refer to either a fixed combination in one dosage unit form, or non-fixed combination, or a kit of parts for the combined administration where two or more therapeutic agents may be administered together, independently at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

By simultaneous therapeutic use, within the meaning of the present invention is meant an administration of at least two active ingredients by the same route and at the same time or at substantially the same time.

By separate use, within the meaning of the present invention is meant in particular an administration of at least two active ingredients at the same time or at substantially the same time by different routes.

By sequential therapeutic use is meant administration of at least two active ingredients at different times, the administration route being identical or different. More particularly by an administration method is meant according to which the whole administration of one of the active ingredients is carried out before administration of the other or others commences.

The terms "fixed combination", "fixed dose" and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents along with any pharmaceutically acceptable carriers or excipients. In some embodiments, the vehicle is a tablet, capsule, pill, or a patch. In other embodiments, the vehicle is a solution or a suspension.

The term "non-fixed combination" or "kit of parts" means that the therapeutic agents of the combination of the invention are both administered to a patient as separate entities either simultaneously, concurrently or sequentially with no specific time limits, wherein such administration provides therapeutically effective levels of the two compounds in the body of a subject in need thereof. The latter also applies to cocktail therapy, e.g., the administration of three or more active ingredients.

The term "pharmaceutically acceptable" as used herein refers to those compounds, materials, compositions and/or dosage forms, which are, within the scope of sound medical judgment, suitable for contact with the tissues of a subject, e.g., a mammal or human, without excessive toxicity, irritation, allergic response and other problems or complications commensurate with a reasonable benefit/risk ratio.

As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art. Except insofar as any conventional carrier is incompatible with the active ingredient, its use in the therapeutic or pharmaceutical compositions is contemplated.

The term "pharmaceutical composition" is defined herein to refer to a mixture or solution containing at least one therapeutic agent to be administered to a subject, e.g., a mammal or human, in order or treat a particular disease or condition affecting the subject. The present pharmaceutical combinations can be formulated in suitable pharmaceutical compositions for enteral or parenteral administration, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units. The pharmaceutical composition may contain, from about 0.1% to about 99.9%, preferably from about 1% to about 60%, of the therapeutic agent(s). One of ordinary skill in the art may select one or more of the aforementioned carriers with respect to the particular desired properties of the dosage form by routine experimentation and without any undue burden. The amount of each carriers used may vary within ranges conventional in the art. The following references disclose techniques and excipients used to formulate oral dosage forms: The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003). These optional additional conventional carriers may be incorporated into the oral dosage form either by incorporating the one or more conventional carriers into the initial mixture before or during granulation or by combining one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Pharmaceutical compositions may be presented in unit dose forms containing a predetermined amount of active ingredient per unit dose. In certain embodiments, the unit dose includes one or more vehicles such that each vehicle includes an effective amount of at least one of the therapeutic agents along with pharmaceutically acceptable carriers and excipients. In some embodiments, the unit dose is one or more tablets, capsules, pills, injections, infusions, patches, or the like, administered to the patient at the same time. As is known to those skilled in the art, the amount of active ingredient per dose will depend on the condition being treated, the route of administration and the age, weight and condition of the patient. Preferred unit dosage compositions are those containing a daily dose or sub-dose, or an appropriate fraction thereof, of an active ingredient. Furthermore, such pharmaceutical compositions may be prepared by any of the methods well known in the pharmacy art.

The pharmaceutical compositions of the invention may include a "therapeutically effective amount" or "effective amount" of a compound of the invention. The term "pharmaceutically effective amount", "therapeutically effective amount" or "clinically effective amount" of a combination of therapeutic agents is an amount sufficient, at dosages and for periods of time necessary, to provide an observable or clinically significant improvement over the baseline of clinically observable signs and symptoms of the disorders treated with the combination. A therapeutically effective amount may vary according to factors such as the disease state, age, sex, and weight of the individual. A therapeutically effective amount is also one in which any toxic or detrimental effects of the therapeutic agents are outweighed by therapeutically beneficial effects. A "therapeutically effective dosage" preferably modulates a measurable parameter, such as tumor growth rate or disease progression in a desired manner. The ability of a compound to modulate a measurable parameter can be evaluated in an animal model system predictive of efficacy in human tumors to help establish suitable dosing levels and schedules. Alternatively, this property of a composition can be evaluated by examining the ability of the compound to modulate an undesired parameter by using in vitro assays known to the skilled practitioner.

The term "jointly therapeutically active" or "joint therapeutic effect" as used herein means that the therapeutic agents can be given jointly, separately or sequentially in such time intervals that they prefer such that the subject, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

As used herein the term "agent" is understood to mean a substance that produces a desired effect in a tissue, system, animal, mammal, human, or other subject. It is also to be understood that an "agent" may be a single compound or a combination or composition of two or more compounds.

The term "proliferative disease" is preferably a cancer.

As used herein, the term "cancer" refers to a disease characterized by the undesired and uncontrolled growth of aberrant cells. Cancer cells can spread locally or through the bloodstream and lymphatic system to other parts of the body. As used herein, the term "cancer" or "tumor" includes premalignant, as well as malignant cancers and tumors. The term "cancer" is used herein to mean a broad spectrum of tumors, including all solid and hematological malignancies.

An "oral dosage form" includes a unit dosage form prescribed or intended for oral administration.

As used herein, the terms "treat", "treatment" and "treating" refer to the reduction or amelioration of the progression, severity and/or duration of a disorder, e.g., a proliferative disorder, or the amelioration of one or more symptoms, suitably of one or more discernible symptoms, of the disorder resulting from the administration of one or more therapies. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent, delay, or treat, or all, as appropriate, development, continuance or aggravation of a disease in a subject, e.g., a mammal or human.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In a preferred embodiment, the subject is a human, e.g., a human suffering from, at risk of suffering from, or potentially capable of suffering from a proliferative disease, such as cancer.

The term "inhibition", "inhibitor," or "antagonist" includes a reduction in a certain parameter, e.g., an activity, of a given molecule or pathway. For example, inhibition of an activity of a targeted kinase (Raf or MEK) by 5%, 10%, 20%, 30%, 40% or more is included by this term. Thus, inhibition may be, but need not be, 100%.

As used herein, "salts" (which, what is meant by "or salts thereof" or "or a salt thereof"), can be present alone or in mixture with free compounds of the combination of the invention, e.g., Raf inhibitor Compound with formula (I) or Raf inhibitor Compound with formula (II) or MEK inhibitor, preferably trametinib, and are preferably pharmaceutically acceptable salts. Such salts are formed, for example, as acid addition salts, preferably with organic or inorganic acids, from compounds of the combination of the invention with a basic nitrogen atom, especially the pharmaceutically acceptable salts. The term "pharmaceutically acceptable salts" refers to salts that retain the biological effectiveness and properties of the compound and which typically are not biologically or otherwise undesirable. The compound may be capable of forming acid addition salts by virtue of the presence of an amino group.

Lists of suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds is to be understood as referring also to the corresponding salts, as appropriate and expedient. The salts of compounds used in the combination of the invention are preferably pharmaceutically acceptable salts; suitable counter-ions forming pharmaceutically acceptable salts are known in the field. Unless otherwise specified, or clearly indicated by the text, reference to therapeutic agents useful in the pharmaceutical combination provided herein includes both the free base of the compounds, and all pharmaceutically acceptable salts of the compounds.

As used herein, the term "solvate" refers to a complex of variable stoichiometry formed by a solute (in this invention, trametinib) or a salt thereof and a solvent. Such solvents for the purpose of the invention may not interfere with the biological activity of the solute. Examples of suitable solvents include, but are not limited to, water, methanol, dimethylsulforide, ethanol and acetic acid. Examples of suitable pharmaceutically acceptable solvents include, without limitation, water, ethanol and acetic acid.

The term "synergistic effect" as used herein, refers to action of two agents such as, for example, Raf inhibitor Compound with formula (I), or a pharmaceutically acceptable salt thereof, and a MEK inhibitor, preferably trametinib, or a pharmaceutically acceptable salt thereof, or Raf inhibitor Compound with formula (II), or a pharmaceutically acceptable salt thereof, and a MEK inhibitor, preferably trametinib, or a pharmaceutically acceptable salt thereof, to produce an effect, for example, slowing the symptomatic progression of cancer or symptoms thereof, which is greater than the simple addition of the effects of each drug administered by themselves.

In one embodiment, the combination of the invention comprises (a) a Raf inhibitor compound selected from the group consisting of (i) Compound of formula (I)

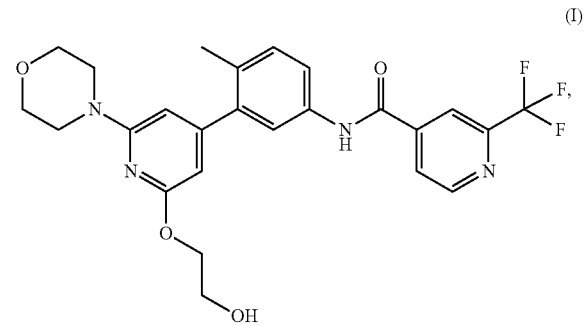 [SMILES: Cc1ccc(NC(=O)c2ccnc(C(F)(F)F)c2)cc1-c1cc(OCCO)nc(N2CCOCC2)c1]

(I)

or a pharmaceutically acceptable salt thereof, and (ii) Compound of formula (II)

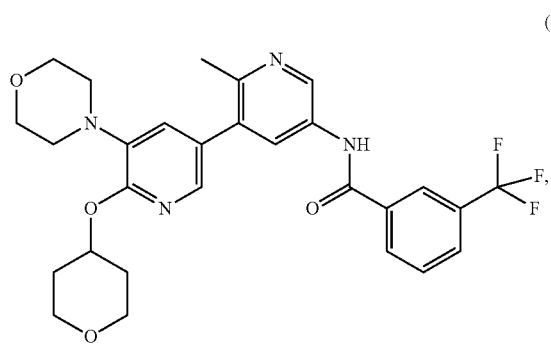

(II)

or a pharmaceutically acceptable salt thereof and (b) a MEK inhibitor.

In one embodiment, the combination of the invention comprises (a) a Raf inhibitor Compound of formula (I)

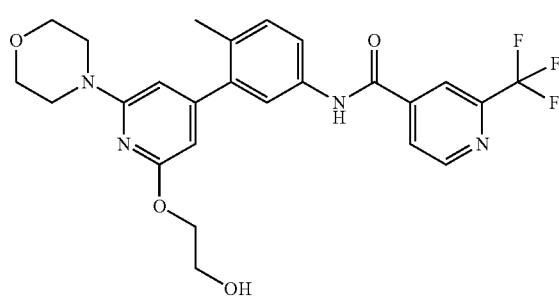

(I)

or a pharmaceutically acceptable salt thereof, and (b) a MEK inhibitor.

In one embodiment, the combination of the invention comprises (a) a Raf inhibitor Compound of formula (II)

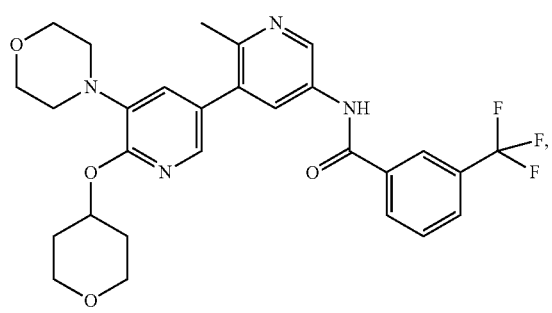

(II)

or a pharmaceutically acceptable salt thereof, and (b) a MEK inhibitor.

In one embodiment, the combination of the invention comprises (a) a Raf inhibitor Compound of formula (I)

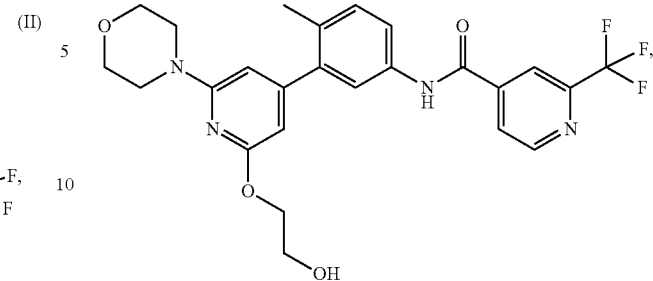

(I)

or a pharmaceutically acceptable salt thereof, and (b) a MEK inhibitor selected from the group comprising trametinib, PD0325901, PD184352, Refametinib, Cobimetinib, AS-701255, AS-701173, Pimasertib, RDEA436, R04987655, RG 7167 and RG7420, or a pharmaceutically acceptable salt or solvate thereof.

In one embodiment, the combination of the invention comprises (a) a Raf inhibitor Compound of formula (II)

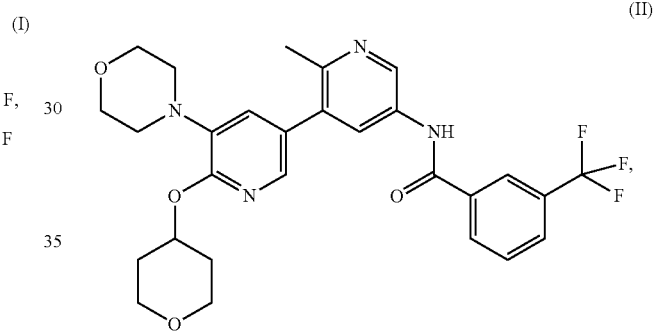

(II)

or a pharmaceutically acceptable salt thereof, and (b) a MEK inhibitor selected from the group comprising trametinib, PD0325901, PD184352, Refametinib, Cobimetinib, AS-701255, AS-701173, Pimasertib, RDEA436, R04987655, RG 7167 and RG7420, or a pharmaceutically acceptable salt or solvate thereof.

In a preferred embodiment, the combination of the invention comprises (a) a Raf inhibitor compound selected from the group consisting of (i) Compound of formula (I)

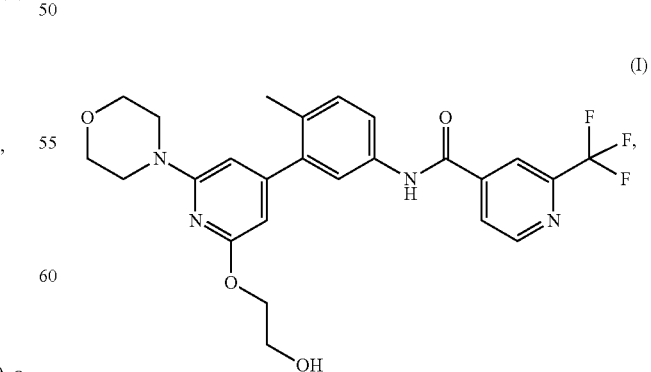

(I)

or a pharmaceutically acceptable salt thereof, and (ii) Compound of formula (II)

(II)

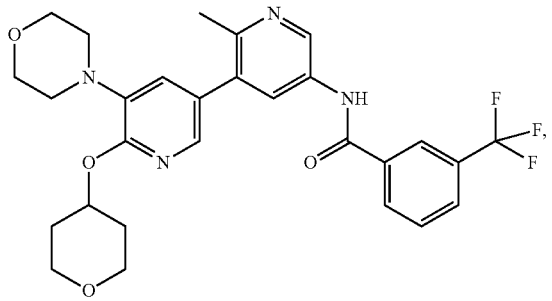

or a pharmaceutically salt thereof and (b) MEK inhibitor trametinib, or a pharmaceutically acceptable salt or solvate thereof.

In a very preferred embodiment, the combination of the invention comprises (a) a Raf inhibitor Compound of formula (I)

(I)

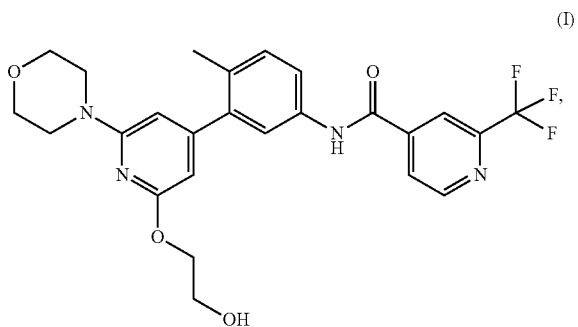 [SMILES: Cc1ccc(NC(=O)c2ccnc(C(F)(F)F)c2)cc1-c1cc(OCCO)nc(N2CCOCC2)c1]

or a pharmaceutically acceptable salt thereof, and (b) MEK inhibitor trametinib, or a pharmaceutically acceptable salt or solvate (e.g. the dimethyl sulfoxide solvate) thereof.

In another preferred embodiment, the combination of the invention comprises (a) a Raf inhibitor Compound of formula (II)

(II)

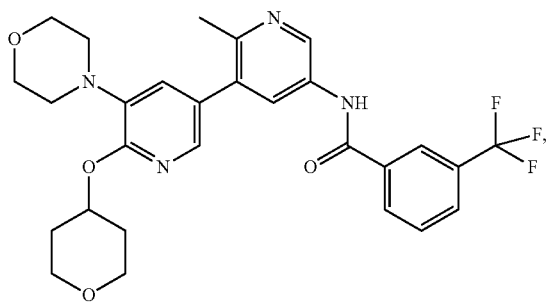

or a pharmaceutically acceptable salt thereof, and (b) MEK inhibitor trametinib, or a pharmaceutically acceptable salt or solvate thereof.

Combinations of the invention demonstrated increased depth and durability of tumor response compared to either single-agent therapy in cell lines and human xenograft models, Calu-6 (see Examples), and may therefore be effective for the treatment of proliferative disease, particularly a cancer. Accordingly, the invention provides compositions and methods using a Raf inhibitor selected from the group consisting of Compound of formula (I), or a pharmaceutically acceptable salt thereof, and Compound of formula (II), or a pharmaceutically acceptable salt thereof, in combination with a MEK inhibitor, and in particular with trametinib, or a pharmaceutically acceptable salt or solvate thereof, for treating solid tumors, particularly tumors that harbor one or more MAPK pathway alterations, e.g. BRAF-mutant, KRAS-mutant and NRAS-mutant cancers.

Preferably, these therapeutic agents are administered at therapeutically effective dosages which, when combined, provide a beneficial effect. The present invention particularly pertains to a combination of the invention useful for separate, simultaneous or sequential administration to a subject in need thereof for treating a proliferative disease. Alternatively stated, the present invention particularly pertains to a combination of the invention for use in the treatment of a proliferative disease.

The nature of proliferative disease is multifactorial. Under certain circumstances, therapeutic agents with different mechanisms of action may be combined. However, just considering any combination of therapeutic agents having different mode of action does not necessarily lead to combinations with advantageous effects.

In the present invention, the administration of the combination of the invention is expected to result in a more beneficial effect, e.g., a synergistic or improved anti-proliferative effect, e.g., with regard to the delay of progression or inhibiting the proliferative disease or its symptoms, and maybe also further beneficial effects, e.g., fewer side-effects, e.g., an improved quality of life or e.g., decreased morbidity, as compared to either monotherapy.

The therapeutic agents of the combination of the invention may be separately, simultaneously or sequentially administered to a subject in need thereof. Preferably, these therapeutic agents are administered at therapeutically effective dosages which, when combined, provide a beneficial effect. Thus, in one embodiment of the present invention, the combination of the invention is for use in the treatment of a proliferative disease, particularly a cancer.

In one embodiment, the proliferative disease is a cancer. The term "cancer" is used herein to mean a broad spectrum of tumors, including all solid and hematological malignancies. The cancer may be at an early, intermediate or late stage. The cancer may be locally advanced or metastatic.

The cancer to be treated by the combination therapy described herein may have progressed following standard of care or for whom no effective standard therapy exists.

The cancer to be treated by the combinations described herein may no longer respond to treatment with BRAF inhibitors such as vemurafenib, dabrafenib and/or MEK inhibitors such as cobimetinib and trametinib. For example, the cancer may be melanoma, e.g. BRAFV600-mutant (including BRAFV600E-mutant) melanoma which is refractory to treatment with a combination of dabrafenib and trametinib or which is refractory to treatment with a combination of cobimetinb and vemurafenib. The NSCLC, e.g. BRAFV600-mutant (including BRAFV600E-mutant) NSCLC, to be treated by the combinations described herein may be refractory to treatment with a combination of BRAF inhibitors such as dabrafenib and MEK inhibitors such as trametinib.

In one embodiment the cancer is selected from the group comprising melanoma, non-small-cell lung cancer (NSCLC), colorectal cancer (CRC) including MUTYH-associated polyposis (MAP), pancreatic ductal adenocarcinoma (PADC), cervical cancer and ovarian cancer.

In one embodiment, the proliferative disease is non-small cell lung cancer (NSCLC).

In one embodiment, the proliferative disease is melanoma.

In one embodiment, the proliferative disease is colorectal cancer (CRC), including MUTYH-associated polyposis (MAP).

In one embodiment, the proliferative disease is pancreatic ductal adenocarcinoma (PADC).

In one embodiment, the proliferative disease is cervical cancer.

In one embodiment, the proliferative disease is ovarian cancer.

The combination of the invention is particularly useful for the treatment of a proliferative disease such as a cancer that harbors one or more Mitogen-activated protein kinase (MAPK) pathway alterations, such as KRAS-mutant tumors and NRAS-mutant tumors, and in particular, tumors expressing at least one gain-of-function mutation of Ras, as described herein, and/or at least one gain-of-function mutation of Raf, as described herein.

Included are cancers or tumors having BRAF mutations, including V600D. V600E, V600K and others, e.g., NSCLC having at least one V600E or other BRAF mutation, whether typical or atypical, i.e. BRAFV600E-mutant NSCLC or BRAF non-V600E-mutant NSCLC. Most of the BRAF mutations are clustered to two regions: the glycine-rich P loop of the N lobe and the activation segment and flanking regions. V600E mutation has been detected in a variety of cancers, and is due to a substitution of thymine with adenine at nucleotide 1799. This leads to valine (V) being substituted for by glutamate (E) at codon 600 (now referred to as V600E). BRAF-mutant melanoma includes BRAFV600E-mutant and BRAFV600D-mutant melanoma.

Included are KRAS-mutant cancers or tumors. The term "KRAS-mutant" tumor or cancer includes any tumor that exhibits a mutated KRAS protein, in particular gain of function KRAS-mutation; especially any G12X, G13X, Q61X or A146X KRAS-mutant, where X is any amino acid other than the one naturally occurring at that position. E.g., a G12V mutation means that a Glycine is substituted with Valine at codon 12. Examples of KRAS mutations in tumors include Q61H, Q61K, G12V, G12C, G12D, G12R, G12S, G13D, and A146T. Thus KRAS-mutant NSCLC includes tumors having at least one KRAS mutation corresponding to G12X, G13X, Q61X or A146X, particularly at least one KRAS mutation selected from Q61K, G12V, G12C and A146T NSCLC. The cancer may be at an early, intermediate or late stage.

KRAS-mutant cancers include KRAS G12D-mutant ovarian cancer; KRAS G12V-mutant or G13D-mutant colorectal cancer; KRAS Q61H-mutant, KRAS Q61K-mutant, KRAS G12C-mutant, KRAS G12S-mutant or KRAS G12V-mutant NSCLC; KRAS G12D-mutant, G12V-mutant, or KRAS G12R-mutant pancreatic cancer.

Included are NRAS mutant cancers or tumors. The term "NRAS-mutant" tumor or cancer includes any tumor that exhibits a mutated NRAS protein, in particular gain of function NRAS-mutation; especially any G13R, Q61K, Q61L, Q61R, NRAS-mutant tumor. Thus NRAS-mutant melanoma includes melanoma having at least one NRAS mutation corresponding to Q61K, Q61L or Q61R. The cancer may be NRAS QG13R-mutant melanoma. The cancer may be at an early, intermediate or late stage. The cancer may be locally advanced or metastatic.

In one embodiment of the invention, the cancer is characterized by one or more mutation in B-Raf.

In another embodiment cancer is resistant or refractory to standard of care.

In another embodiment cancer is resistant or refractory to treatment with a B-Raf inhibitor, e.g. dabrafenib.

In another embodiment cancer is resistant or refractory to treatment with a MEK inhibitor, e.g. trametinib.

In another embodiment cancer is resistant or refractory to treatment with a B-Raf inhibitor, e.g. dabrafenib, and a MEK inhibitor, e.g. trametinib.

In one embodiment, the cancer is characterized by at least one mutation selected from the group comprising BRAF and KRAS proteins.

In one embodiment, the cancer is characterized by a mutation selected from the group consisting of BRAF, NRAS, KRAS mutation and combinations thereof.

In one embodiment, the combination of the invention relates to a method for treating a proliferative disease, particularly a cancer.

The combination of the invention may be especially useful in treating KRAS-mutant NSCLC, KRAS-mutant pancreatic cancer, KRAS-mutant colorectal cancer, or NRAS-mutant melanoma. In a preferred embodiment, the proliferative disease or the cancer to be treated is KRAS-mutant NSCLC. In another preferred embodiment, the proliferative disease or the cancer to be treated is NRAS-mutant melanoma.

In one embodiment, provided herein is a method for treating cancer in a subject in need thereof comprising administering a therapeutically effective amount of a pharmaceutical combination of the invention comprising (a) a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, and (b) a MEK inhibitor. In a preferred embodiment, the MEK inhibitor is trametinib, or a pharmaceutically acceptable salt or solvate thereof.

In an embodiment, provided herein is a method for treating cancer in a subject in need thereof administering simultaneously, separately or sequentially to a subject in need thereof a combination of the invention in a quantity which is jointly therapeutically effective against said proliferative disease comprising (a) a Raf inhibitor selected from the group consisting of (i) Compound of formula (I), as defined herein, or a pharmaceutically acceptable salt thereof and (ii) Compound of formula (II), as defined herein, or a pharmaceutically acceptable salt thereof, and (b) a MEK inhibitor. In a preferred embodiment, the MEK inhibitor is trametinib, or a pharmaceutically acceptable salt or solvate thereof.

In a further embodiment, the present invention is particularly related to a method of treating a cancer harboring one or more Mitogen-activated protein kinase (MAPK) pathway alterations. In one embodiment, the present invention is related to a method of treating a cancer, which is characterized by at least one mutation selected from the group comprising BRAS, NRAS and KRAS proteins. In one embodiment, the present invention relates to the use of the combination of the invention for the preparation of a medicament for the treatment of a proliferative disease, particularly a cancer. In one embodiment, the combination of the invention is for use in the preparation of a medicament for the treatment of cancer.

In a further embodiment, the present invention relates to the use of the combination of the invention for the preparation of a medicament for the treatment of a cancer characterized by gain-of-function mutation in the MAPK pathway.

In an embodiment, the combination or composition, or both, provided herein display a synergistic effect.

Accordingly, in one aspect, the invention may provide a method of enhancing the efficacy of an anticancer compound by using it in combination with another anticancer compound, particularly a method using a Raf inhibitor selected from the group consisting of (i) Compound of formula (I), as defined herein, or a pharmaceutically acceptable salt thereof, and (ii) Compound of formula (II), as defined herein, or a pharmaceutically acceptable salt thereof, together with a MEK inhibitor, suitably trametinib, or a pharmaceutically acceptable salt or solvate thereof, to provide enhanced efficacy not safely achievable by administering similar doses of either Compound of formula (I), or a pharmaceutically acceptable salt thereof, or Compound (II), or a pharmaceutically acceptable salt thereof, or the MEK inhibitor as a single agent (monotherapy).

A further benefit may be that lower doses of the therapeutic agents of the combination of the invention can be used, for example, such that the dosages may not only often be smaller, but also may be applied less frequently, or can be used in order to diminish the incidence of side-effects observed with one of the combination partners alone. This is in accordance with the desires and requirements of the patients to be treated.

In some embodiments, the Raf inhibitor compound selected from the group consisting of (i) Compound of formula (I), as defined herein, or a pharmaceutically acceptable salt thereof, and (ii) Compound of formula (II), as defined herein, or a pharmaceutically acceptable salt thereof, or a pharmaceutically acceptable salt thereof, and/or the MEK inhibitor, preferably trametinib, or a pharmaceutically acceptable salt or solvate thereof, may be administered at a therapeutic or lower-than therapeutic dose relative to a single-agent dose level. In certain embodiments, the concentration or dosage of the one therapeutic agent that is required to achieve inhibition, e.g., growth inhibition or tumor shrinkage is lower when the other therapeutic agent is used or administered in combination with the first therapeutic agent than when each therapeutic agent is administered individually. In certain embodiments, in a combination therapy, the concentration or dosage of one therapeutic agent that is required to achieve inhibition, e.g., growth inhibition, is lower than the therapeutic dose as a monotherapy, e.g., 10-20%, 20-30%, 30-40%, 40-50%, 50-60%, 60-70%, 70-80%, or 80-90% lower.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render the use of this form of testing as a primary model for synergy impractical. However, the observation of synergy in certain experiments (see, e.g., Example 2 and Example 6) can be predictive of the effect in other species, and animal models exist may be used to further quantify a synergistic effect. The observation of synergy in one species can be predictive of the effect in other species and using animal models, as described herein, a synergistic effect can be measured and the results of such studies can also be used to predict effective dose ratio ranges and the absolute doses and plasma concentrations required in other species by the application of pharmacokinetic/pharmacodynamic (PK/PD) methods. Established correlations between tumor models and effects seen in man suggest that synergy in animals may be demonstrated, for example, by xenograft models or in appropriate cell lines. It can be shown by established test models that a combination of the invention results in the beneficial effects described herein. The person skilled in the art is fully enabled to select a relevant test model to prove such beneficial effects. The pharmacological activity of the combination of the invention may, for example, be demonstrated in a clinical study or in an in vivo or in vitro test procedure as essentially described herein.

Administration of the combination includes administration of the combination in a single formulation or unit dosage form, administration of the individual agents of the combination concurrently but separately, or administration of the individual agents of the combination sequentially by any suitable route. The individual combination partners of the combination of the invention may be administered separately at different times during the course of therapy, or sequentially in any order or concurrently in divided or single combination forms, e.g., simultaneously or in jointly therapeutically effective amounts, preferably in synergistically effective amounts, e.g., in daily or intermittent (i.e., not daily) dosages corresponding to the amounts described herein.

Compound of formula (I), or a pharmaceutically acceptable salt thereof, and Compound of formula (II), or a pharmaceutically acceptable salt thereof, for use in the methods, treatments, combinations and compositions disclosed herein are potent inhibitors of BRAF and CRAF. In some embodiments, Compound of formula (I), or a pharmaceutically acceptable salt thereof, or Compound of formula (II), or a pharmaceutically acceptable salt thereof, is administered orally. In one embodiment, Compound of formula (I), or a pharmaceutically acceptable salt thereof, or Compound of formula (II), or a pharmaceutically acceptable salt thereof, is administered at a dose of about 50-1200 mg (e.g., per day). Compound of formula (I), or a pharmaceutically acceptable salt thereof, or Compound of formula (II), or a pharmaceutically acceptable salt thereof, can be administered at a unit dosage of about 50 mg, about 100 mg, about 150 mg, about 200 mg, about 250 mg, about 300 mg, about 350 mg, about 400 mg, about 450 mg, about 500 mg about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg or about 1200 mg. The unit dosage of Compound of formula (I), or a pharmaceutically acceptable salt thereof, or Compound of formula (II), or a pharmaceutically acceptable salt thereof, may be administered once daily, or twice daily, or three times daily, or four times daily, with the actual dosage and timing of administration determined by criteria such as the patient's age, weight, and gender; the extent and severity of the cancer to be treated; and the judgment of a treating physician. Preferably, the unit dosage of Compound of formula (I) or Compound of formula (II) is administered once daily. In another preferred embodiment, the unit dosage of Compound of formula (I) or Compound of formula (II) is administered twice daily.

The MEK inhibitor as part of the combination according to the present invention will be administered to a subject in need thereof in a therapeutically effective amount.

In a preferred embodiment, the MEK inhibitor trametinib, or a pharmaceutically acceptable salt or solvate thereof, administered as part of the combination according to the present invention in a subject in need thereof will be an amount selected from about 0.125 mg to about 10 mg per day; suitably, the amount will be selected from about 0.25 mg to about 9 mg per day; suitably, the amount will be selected from about 0.25 mg to about 8 mg; suitably, the amount will be selected from about 0.5 mg to about 8 mg per day; suitably, the amount will be selected from about 0.5 mg to about 7 mg per day; suitably, the amount will be selected from about 1 mg to about 5 mg per day; suitably, the amount will be about 1 mg or 2 mg per day. In a preferred embodiment, trametinib, trametinib, or a pharmaceutically acceptable salt or solvate thereof, is administered at daily dose of 0.5 mg, 1 mg or 2 mg per day.

Where doses or dosages are mentioned herein, the amount referred to refers to the amount of the therapeutic agent. For example, when a 2 mg dosage of trametinib is administered, and trametinib is administered in a tablet containing trametinib dimethyl sulfoxide, the tablet will contain trametinib dimethyl sulfoxide equivalent to 2 mg trametinib.

In some embodiments, trametinib, or a pharmaceutically acceptable salt or solvate thereof, is administered orally. In one embodiment, trametinib is prepared for administration via oral delivery, and may be used in solvated form in dimethyl sulfoxide. In some embodiments, the compound is prepared in tablet form for oral administration. The tablets can be produced in a variety of dosages for flexible administration.

The unit dosage of trametinib, or a pharmaceutically acceptable salt or solvate thereof, may be administered once daily, or twice daily, or three times daily, or four times daily. The total daily dose of trametinib, or a pharmaceutically acceptable salt or solvate thereof, e.g., the dimethyl sulfoxide solvate, may be administered once or twice a day.

For example, as part of the combination therapy, Compound of formula (I), or a pharmaceutically acceptable salt thereof, may be administered at a total daily dose of about 50 mg, about 100 mg, about 200 mg, about 300 mg, about 400 mg, about 500 mg, about 600 mg, or about 800 mg and trametinib, e.g. in the dimethyl sulfoxide solvate form, may be administered in a total daily dose of about 1.0 or 2.0 mg. The daily dose of the Compound of formula (1) may be administered once or twice per day. Hence, a dose of about 200 mg of Compound of formula (I) may be administered twice per day and (total daily dose about 400 mg) and a dose of about 1.0 mg or about 2.0 mg of trametinib may be administered once per day. Alternatively, a dose a dose of about 200 mg of Compound of formula (I) may be administered twice per day and (total daily dose about 400 mg) and a dose of about 1.0 mg or about 2.0 mg of trametinib may be administered twice per day.

Compound of formula (I), or a pharmaceutically acceptable salt thereof, and a MEK inhibitor, preferably trametinib, or a pharmaceutically acceptable salt or solvate thereof, or Compound of formula (II), or a pharmaceutically acceptable salt thereof, and a MEK inhibitor, preferably trametinib, or a pharmaceutically acceptable salt or solvate thereof, can be used together according to methods disclosed herein. The two compounds can be administered together or separately, depending on the intended dosage amount and frequency of administration, since it is contemplated that the treatments of the invention may be continued for 2 days, 3 days, 4 days, 5 days, 6 days, 1 week, 2 weeks, 3 weeks, 4 weeks, or more than 4 weeks as deemed appropriate to the treating physician, and further as guided using methods described herein to determine a suitable dosage and administration frequency. Frequency of dosage may vary depending on the compound used and the particular condition to be treated. In general, the use of the minimum dosage that is sufficient to provide effective therapy is preferred and may be determined by criteria such as the patient's age, weight, and gender; the extent and severity of the cancer to be treated; and the judgment of a treating physician. Patients may generally be monitored for therapeutic effectiveness using assays suitable for the condition being treated, which will be familiar to those of ordinary skill in the art.

The optimum ratios, individual and combined dosages, and concentrations of the combination partners of the combination of the invention, (i.e., Compound of formula (I), or a pharmaceutically acceptable salt thereof, and a MEK inhibitor, suitably trametinib, or a pharmaceutically acceptable salt or solvate thereof, or Compound of formula (II), or a pharmaceutically acceptable salt thereof, and a MEK inhibitor, suitably trametinib, or a pharmaceutically acceptable salt or solvate thereof, that yield efficacy without toxicity are based on the kinetics of the therapeutic agents' availability to target sites and a variety of factors, including, but not limited to, the degree of advancement of the disease; the age, body weight, general health, gender and diet of the individual; the time and route of administration; and other medications the individual is taking. Optimal dosages may be established using routine testing and procedures that are well known in the art. For example, a single bolus may be administered, several divided doses may be administered over time or the dose may be proportionally reduced or increased as indicated by the exigencies of the therapeutic situation.

The therapeutic agents of the combination of the invention may be administered by any appropriate route. It will be appreciated that the preferred route may vary with, for example, the condition of the recipient of the combination and the cancer to be treated. It will also be appreciated that each of the therapeutic agents may be administered by the same or different routes and that the therapeutic agents, e.g., Compound of formula (I), or a pharmaceutically acceptable salt thereof, and the MEK inhibitor, suitably trametinib, or a pharmaceutically acceptable salt or solvate thereof, or Compound of formula (II), or a pharmaceutically acceptable salt thereof, and the MEK inhibitor, suitably trametinib, or a pharmaceutically acceptable salt or solvate thereof, may be compounded together in a pharmaceutical composition.

Compound of formula (I), or a pharmaceutically acceptable salt thereof, and the MEK inhibitor, suitably trametinib, or a pharmaceutically acceptable salt or solvate thereof, or Compound of formula (II), or a pharmaceutically acceptable salt thereof, and the MEK inhibitor, suitably trametinib, or a pharmaceutically acceptable salt or solvate thereof, can be used together as disclosed herein. The two therapeutic agents of the combination of the invention can be administered together (simultaneously), sequentially or separately.

Furthermore, it does not matter if the compounds are administered in the same dosage form, e.g., one compound may be administered topically and the other compound may be administered orally. Suitably, both therapeutic agents are administered orally.

Thus in one embodiment, one or more doses of Compound of formula (I), or a pharmaceutically acceptable salt thereof, or one or more doses of Compound of formula (II), or a pharmaceutically acceptable salt thereof, are administered simultaneously, sequentially or separately with one or more doses of a MEK inhibitor, suitably trametinib, or a pharmaceutically acceptable salt or solvate thereof.

In one embodiment, multiple doses of Compound of formula (I), or a pharmaceutically acceptable salt thereof, or multiple doses of Compound of formula (II), or a pharmaceutically acceptable salt thereof, are administered simultaneously, sequentially or separately with multiple doses of a MEK inhibitor, suitably trametinib, or a pharmaceutically acceptable salt or solvate thereof.

In one embodiment, multiple doses of Compound of formula (I), or a pharmaceutically acceptable salt thereof, or multiple doses of Compound of formula (II), or a pharmaceutically acceptable salt thereof, are administered simultaneously, sequentially or separately with one dose of a MEK inhibitor, suitably trametinib, or a pharmaceutically acceptable salt or solvate thereof.

In one embodiment, one dose of Compound of formula (I), or a pharmaceutically acceptable salt thereof, or one dose of Compound of formula (II), or a pharmaceutically acceptable salt thereof, is administered simultaneously, sequentially or separately with multiple doses of a MEK inhibitor, suitably trametinib, or a pharmaceutically acceptable salt or solvate thereof.

In one embodiment one dose of Compound of formula (I), or a pharmaceutically acceptable salt thereof, or one dose of Compound of formula (II), or a pharmaceutically acceptable salt thereof, is administered simultaneously, sequentially or separately with one dose of a MEK inhibitor, suitably trametinib, or a pharmaceutically acceptable salt or solvate thereof.

In all the above embodiments Compound of formula (I), or a pharmaceutically acceptable salt thereof, or Compound of formula (II), or a pharmaceutically acceptable salt thereof, may be administered first or the MEK inhibitor, suitably trametinib, or a pharmaceutically acceptable salt or solvate thereof, may be administered first.

While it is possible that, for use in therapy, the Raf inhibitor selected from the group comprising (i) Compound of Formula (I), or a pharmaceutically acceptable salt thereof, and (ii) Compound of Formula (II), or a pharmaceutically acceptable salt thereof, and/or the MEK inhibitor, suitably trametinib, or a pharmaceutically acceptable salt or solvate thereof, may be administered as the raw chemical, it is possible to present the active ingredient as a pharmaceutical composition. Accordingly, in one embodiment, provided herein is a pharmaceutical composition comprising (a) a Raf inhibitor compound selected from the group consisting of Compound of formula (I), or a pharmaceutically acceptable salt thereof, and Compound of formula (II), or a pharmaceutically acceptable salt thereof, and (b) a MEK inhibitor, suitably trametinib, or a pharmaceutically acceptable salt or solvate thereof. In an embodiment, the pharmaceutical composition further comprises one or more pharmaceutically acceptable diluents, excipients or carriers. The carrier(s), diluent(s) or excipient(s) must be acceptable in the sense of being compatible with the other ingredients of the formulation, capable of pharmaceutical formulation, and not deleterious to the recipient thereof. Such elements of the pharmaceutical compositions utilized may be presented in separate pharmaceutical combinations or formulated together in one pharmaceutical composition. The combinations disclosed herein can be administered together in a single composition or administered separately in two or more different compositions, e.g., compositions or dosage forms as described and the components may be administered as the same formulation, or as separate formulations, alone, e.g., as indicated above, or in combination with one or more pharmaceutically acceptable carriers by any suitable route.

Dosage unit form as used herein refers to physically discrete units suited as unitary dosages for the subjects to be treated; each unit contains a predetermined quantity of active compound (e.g., Compound of formula (I), or a pharmaceutically acceptable salt thereof, Compound of formula (II), or a pharmaceutically acceptable salt thereof, or the MEK inhibitor, suitably trametinib, or a pharmaceutically acceptable salt or solvate thereof, calculated to produce the desired therapeutic effect in association with the required pharmaceutical carrier. The unit dosage form may also be a fixed combination.

The effective dosage of each of the combination partners may require more frequent administration of one of the therapeutic agent as compared to the other therapeutic agent in the combination. Therefore, to permit appropriate dosing, packaged pharmaceutical products may contain one or more dosage forms that contain the combination of compounds, and one or more dosage forms that contain one of the therapeutic agents of the combination of the invention, but not the other therapeutic agent of the combination of the invention.

When the combination partners, which are employed in the combination of the invention, are applied in the form as marketed as single drug, their dosage and mode of administration can be in accordance with the information provided on the package insert of the respective marketed drug, if not mentioned otherwise. Therefore, to permit appropriate dosing, packaged pharmaceutical products can contain one or more dosage forms that contain the combination of agents, and one or more dosage forms that contain one of the therapeutic agents of the combination, but not the other therapeutic agent of the combination.

Also within the scope of the invention is a combination kit comprising, as therapeutic agents, the combination of the invention for simultaneous, separate or sequential administration as described herein, together with one or more other elements: instructions for use; other reagents for use with the combination of the invention; devices or other materials for preparing the compound for administration, such as a mixing container; pharmaceutically acceptable carriers; and devices or other materials for administration to a subject, such as a syringe.

By the term "combination kit" or "kit of parts" as used herein is meant the pharmaceutical composition or compositions that are used according to the invention. When both compounds are administered simultaneously, the combination kit can contain Compound of formula (I), or a pharmaceutically acceptable salt thereof, and the MEK inhibitor, suitably trametinib, or a pharmaceutically acceptable salt or solvate thereof, or Compound of formula (II), or a pharmaceutically acceptable salt thereof, and the MEK inhibitor, suitably trametinib, or a pharmaceutically acceptable salt or solvate thereof, in a single pharmaceutical composition, such as a tablet, or in separate pharmaceutical compositions. When Compound of formula (I), or a pharmaceutically acceptable salt thereof, and the MEK inhibitor, suitably trametinib, or a pharmaceutically acceptable salt or solvate thereof, or Compound of formula (II), or a pharmaceutically acceptable salt thereof, and the MEK inhibitor, suitably trametinib, or a pharmaceutically acceptable salt or solvate thereof, are not administered simultaneously, the combination kit will contain Compound of formula (I), or a pharmaceutically acceptable salt thereof, Compound of formula (II), or a pharmaceutically acceptable salt thereof, and the MEK inhibitor, suitably trametinib, or a pharmaceutically acceptable salt or solvate thereof, in separate pharmaceutical compositions either in a single package or in separate pharmaceutical compositions in separate packages.

In one embodiment of the invention the kit of parts comprising the following components: (a) a Raf inhibitor compound selected from the group consisting of (i) Compound of formula (I), or a pharmaceutically acceptable salt thereof, in association with pharmaceutically acceptable excipients, diluents and/or carriers, and (ii) Compound of formula (II), or a pharmaceutically acceptable salt thereof, in association with pharmaceutically acceptable excipients, diluents and/or carriers; and (b) a MEK inhibitor, preferably trametinib, or a pharmaceutically acceptable salt or solvate thereof, in association with a pharmaceutically acceptable excipients, diluents or carrier, wherein the components are provided in a form which is suitable for sequential, separate and/or simultaneous administration. The combination kit can also be provided with instructions, such as dosage and administration instructions. Such dosage and administration instructions can be of the kinds that are provided to a doctor, for example by a drug product label, or they can be of the kinds that are provided by a doctor, such as instructions to a patient.

Other features, objects, and advantages of the invention will be apparent from the description and drawings, and from the claims.

The following Examples illustrate the invention described above; they are not, however, intended to limit the scope of the invention in any way. The beneficial effects of the pharmaceutical combination of the present invention can also be determined by other test models known as such to the person skilled in the pertinent art.

EXAMPLES

The Examples below are set forth to aid in the understanding of the invention but are not intended, and should not be construed, to limit its scope in any way.

Example 1

N-(3-(2-(2-hydroxyethoxy)-6-morpholinopyridin-4-yl)-4-methylphenyl)-2-(trifluoromethyl)isonicotinamide Compound of formula (I) is a morpholine-substituted biaryl compound of the following structure

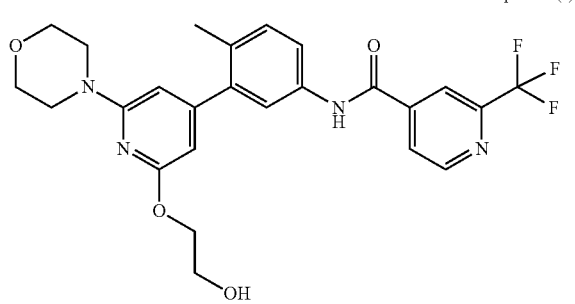

Compound (I)

Compound of formula (I) is Example 1156 in published PCT application WO2014/151616, the contents of which are incorporated by reference.

Example 1A

Compound of formula (I) is a type II inhibitor of both b-Raf and c-Raf.

TABLE 1

| Half maximal inhibitory concentration (IC-50) of Compound of formula (I) on b-Raf and c-Raf | | |
|---|---|---|
| Compound | b-Raf IC-50 (μM) | c-Raf FL IC-50 (μM) |
| Compound of formula (I) | 0.00073 | 0.00020 |

Example 1B

Compound of formula (I) exhibits activity on numerous human cancer cell lines that express mutations in the MAPK pathway as shown in the following Table. Activity is especially strong on cell lines that harbor at least one mutation in BRAF or RAS.

TABLE 2

| Effect of Compound of formula (I) on proliferation in a panel of human cancer cell lines. | | | | |
|---|---|---|---|---|
| Cell Line | $IC_{50}$ [μM] | Tumor Type | BRAF | RAS |
| A375 | 0.24 | Melanoma | V600E | WT |
| WM2664 | 0.45 | Melanoma | V600D | WT |
| IPC298 | 0.25 | Melanoma | WT | NRAS Q61L |
| HeyA8 | 0.21 | Ovarian | G464E | KRAS G12D |
| HCT116 | 0.47 | Colorectal | WT | KRAS G13D |
| Calu-6 | 1.5 | NSCLC | WT | KRAS Q61K |
| HuP-T4 | 0.65 | Pancreas | WT | KRAS G12V |
| PSN1 | 0.68 | Pancreas | WT | KRAS G12R |
| TCC-PAN2 | 0.42 | Pancreas | WT | KRAS G12R |
| NCI-H2073 | 18.2 | NSCLC | WT | WT |
| HCC827 | >20 | NSCLC | WT | WT |
| PC3 | >20 | Prostate | WT | WT |

Different tumor cell lines were treated with dose titrations of Compound of formula (I) for 72 h, and cell proliferation was determined using the CellTiter-Glo ™ luminescent cell viability assay.

Example 1C

To investigate the activity of Compound of formula (I) in B-Raf V600 mutant melanoma cells refractory to B-Raf and/or MEK inhibitors, the anti-proliferative activity of Compound of formula (I) in the mechanistic models derived from the B-Raf V600 melanoma cell line A375 expressing mutations of MEK1/2, NRAS, or a splice variant of BRAF was evaluated. These mutations have been demonstrated in both preclinical studies and clinical samples to confer B-Raf and/or MEK inhibitor resistance. Growth inhibitory effects of Compound of formula (I) in the parental A375 cell line and its derivatives expressing the various mutant alleles, in comparison with efficacy of the B-Raf inhibitor vemurafenib and the MEK inhibitor selumetinib, are summarized below. The mutations conferred resistance to both the B-Raf and MEK inhibitors, leading to greater than 50-fold increases in $IC_{50}$ values. In contrast, the resistant models were still sensitive to Compound of formula (I), with only a 2-3 fold increase in $IC_{50}$. These data support the use of Compound of formula (I) in B-Raf V600 melanoma patients who have become refractory to B-Raf and/or MEK inhibitors.

TABLE 3

Anti-proliferative effect of Compound of formula (I) in mechanistic A375 models resistant to BRAF and MEK inhibitors

| Cell Line | Compound of formula (I) IC$_{50}$ [μM] | Vemurafenib IC$_{50}$ [μM] | Selumetinib IC$_{50}$ [μM] |
|---|---|---|---|
| A375 | 0.42 | 0.066 | 0.036 |
| A375/BRAFp61-V600E | 0.72 | 8.51 | >10 |
| A375/MEK1 Q56P | 1.15 | 9.62 | 5.35 |
| A375/MEK1 C121S | 1.14 | 8.7 | 2.33 |
| A375/MEK1 E203K | 1.05 | 5.58 | 1.81 |
| A375/MEK2 Q60P | 1.12 | 5.28 | 4.84 |
| A375/NRAS Q61K | 0.95 | 9.38 | 5.5 |

A375 cell lines were engineered to inducibly express resistance models after treatment with doxycycline. Cell were then treated with serial dilutions of Compound of formula (I), vemurafenib or selumetinib for 72 hours to assess anti-proliferative activity. Cell proliferation was determined using the CellTiter-Glo ™ luminescent cell viability assay and calculated as percent of DMSO control.

Example 1D

Compound of formula (I) was formulated for oral dosing into tablets containing about 50 mg of Compound of formula (I) according to principles well known in the art. A number of tablets sufficient to provide a desired dosage were administered once daily to fasted subjects. Subjects were treated at doses of 100 mg once per day, or 200 mg once per day. Serial blood samples for pharmacokinetic (PK) assessments were collected up to 48 hours after the first dose of Compound of formula (I) (Cycle 1 Day 1), and up to 24 hours after multiple doses (Cycle 1 Day 15). Preliminary available data are as follows. Maximum plasma concentrations (Cmax) of 447 ng/ml and 889 ng/ml were achieved within 4 hours after administration of a single 100 mg dose and single 200 mg dose, respectively. Mean plasma exposure over the dose interval of 24 hours (AUCtau) on day 1 of dosing was 5679 hr.ng/ml and 10019 hr.ng/ml after the 100 mg and 200 mg doses of Compound of formula (I), respectively. The half-life is calculated to be around 23-24 hours in patients. The once daily dosing of 100 mg resulted in slight accumulation of Compound of formula (I) in plasma, with an accumulation ratio of 1.8. Based on these data, a dosing schedule of once per day was established.

Example 2

Anti-Tumor Activity of Compound of Formula (I) in KRAS-Mutant NSCLC Models

In cell-based assays, Compound of formula (I) has demonstrated anti-proliferative activity in cell lines that contain a variety of mutations that activate MAPK signaling. For instance, Compound of formula (I) inhibited the proliferation of the non-small cell lung cancer cell line Calu-6 (KRAS Q61K) and colorectal cell line HCT116 (KRAS G13D) with IC50 values ranging from 0.2-1.2 μM.

Activity of Compound of formula (I) was tested in vivo in several xenograft models. As shown in FIGS. 1-4, Compound of formula (I) showed single agent activity in KRAS mutant lung cancer models.

Figure 1:
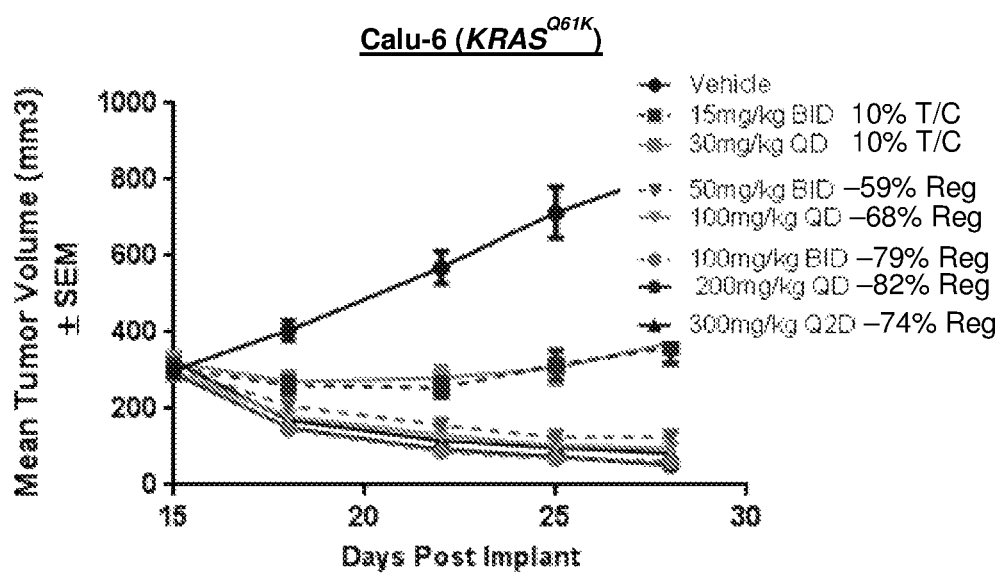
FIGS. 1-4. Compound of formula (I) in FIG. 1) Calu-6 (KRAS(Q61K) mutant), FIG. 2) NCI-H358 (KRAS(G12C) mutant), FIG. 3) HLUX1156 (KRAS(G12C) mutant) and FIG. 4) NCI-H727 (KRAS(G12V) mutant) xenograft lung cancer tumor models in mice. Animals with subcutaneous xenografts received treatment with Compound of formula (I) as indicated. Compound was administered orally (PO) either daily (qd or QD), twice daily (bid or BID) or every other day (q2d or Q2D) as indicated. Anti-tumor activity was determined by assessing percentage of tumor volume in the treatment groups versus that in vehicle-treated group (% T/C) or percentage of tumor regression (i.e., volume of tumor after treatment compared to the starting volume (% regression) (indicated as "% Reg" or "−% Reg" in FIGS. 1-4). SEM=standard error of the mean, PBS=phosphate buffered saline.

Calu6 model (KRAS(Q61K) mutant NSCLC): Female nude tumor bearing Calu6 mice, n=8 per group were randomized into treatment groups when the average tumor volume was 324 mm3. Treatment with Compound of formula (I) was initiated on Day 15 post xenograft implant. Animals were administered an oral dose of either vehicle, Compound of formula (I) at 15 mg/kg twice a day (bid), 30 mg/kg once a day (qd), 50 mg/kg bid, 100 mg/kg bid, 200 mg/kg qd or 300 mg/kg every other day (q2d) for 13 consecutive days at a dosing volume of 10 ml/kg of animal body weight during course of treatment. Tumor volumes were collected at the time of randomization and twice weekly thereafter for the study duration using digital calipers (FIG. 1). Slight body weight loss was observed in the 200 mg/kg qd (4% body weight loss) and 300 mg/kg q2d (9% body weight loss) treatment groups.

H358 model (KRAS(G12C) mutant NSCLC): SCID beige female tumor-bearing NCI-H358 mice, n=8 per group, were randomized into 3 groups 14 days post tumor cell inoculation with an average tumor volume range of 261 mm$^3$.

Figure 2:
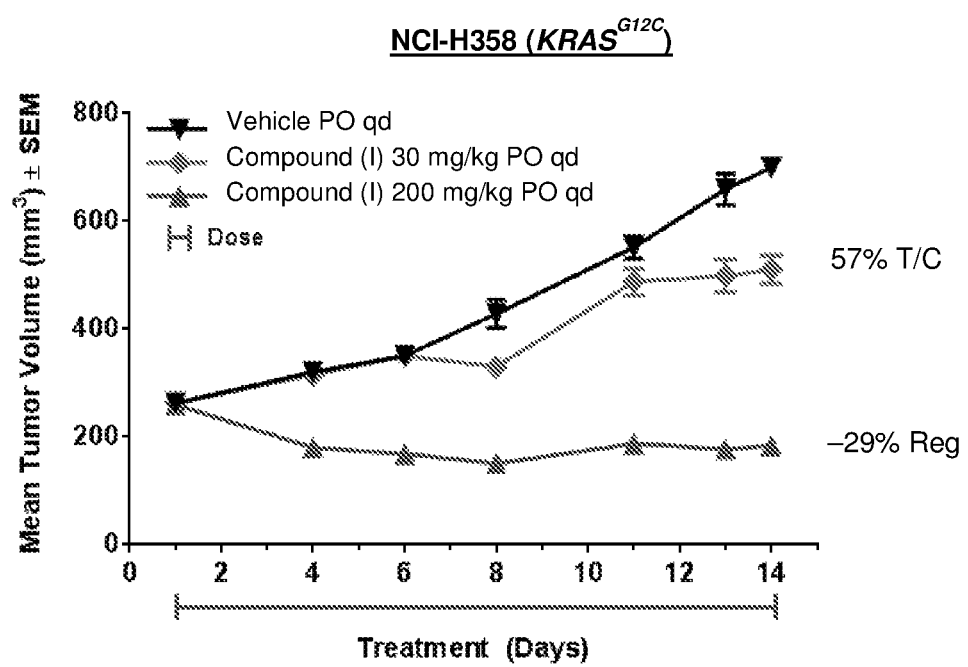

Animals were administered an oral dose of either vehicle, Compound of formula (I) at 30 mg/kg or at 200 mg/kg daily for 14 consecutive days at a dosing volume of 10 ml/kg of animal body weight during course of treatment. Tumor volumes were measured by digital caliper 3 times a week and body weights of all animals were recorded through the course of treatment (FIG. 2). Slight body weight loss was observed in the 30 mg/kg (4% body weight loss) and 200 mg/kg (6% body weight loss) treatment groups.

Figure 3:
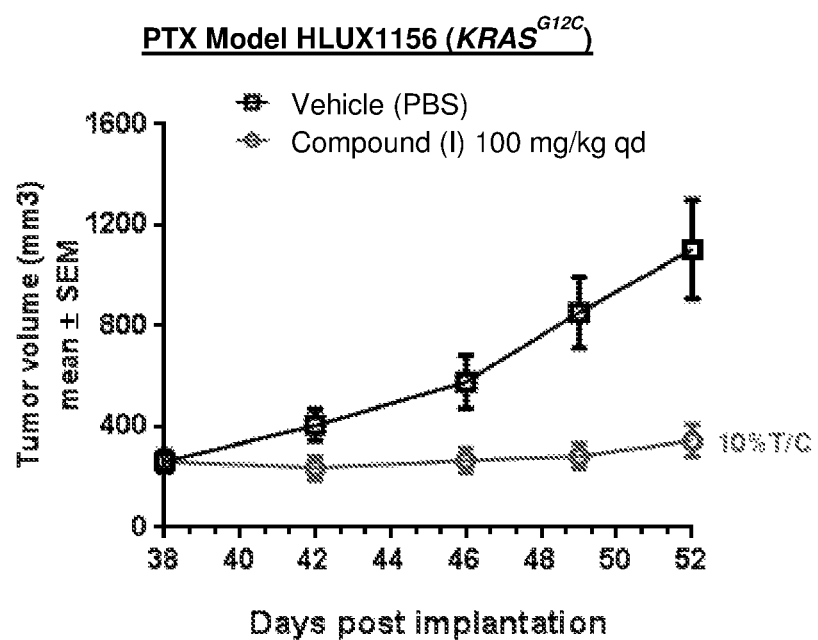

PTX model HLUX1156-KRAS(G12C) mutant NSCLC: Nude female mice tumor bearing patient derived primary lung cancer xenograft HLUX1156, n=6 per group, were randomized into 2 groups with an average tumor volume range of 262 mm3. Treatment was initiated on Day 38 post xenograft implant. Animals were administered an oral dose of either vehicle or Compound of formula (I) at 100 mg/kg daily for 14 consecutive days at a dosing volume of 10 ml/kg of animal body weight during course of treatment. Tumor volumes were measured by digital caliper 2 times a week and body weights of all animals were recorded through the course of treatment (FIG. 3). Treatment was well tolerated as judged by lack of significant body weight loss.

Figure 4:
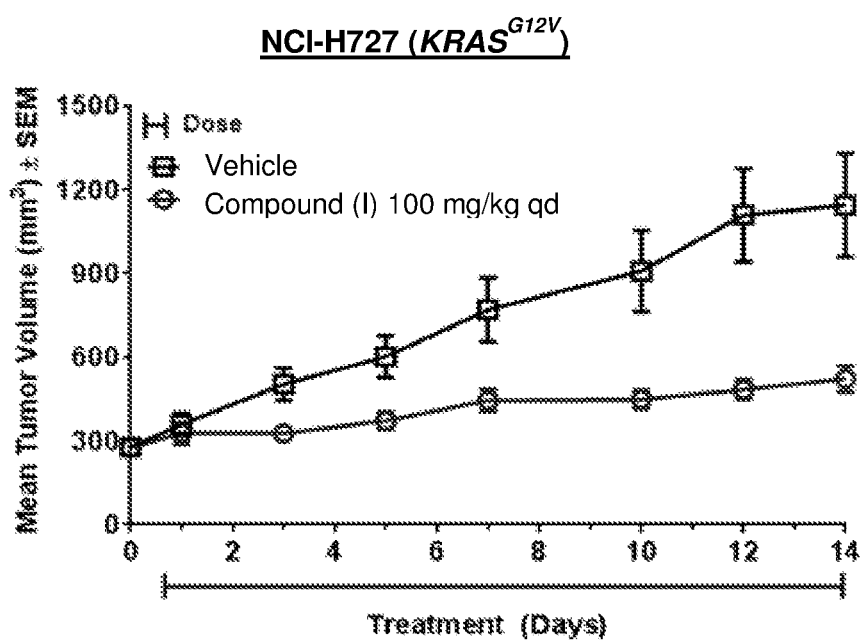

H727 model-KRAS(G12V) mutant NSCLC: Foxn1 nude female mice tumor bearing NCI-H727, n=8 per group, were randomized into 2 groups with an average tumor volume range of 275 mm3. Treatment was initiated on Day 21 post xenograft implant. Animals were administered an oral dose of either vehicle or Compound of formula (I) at 100 mg/kg daily for 14 consecutive days at a dosing volume of 10 ml/kg of animal body weight during course of treatment. Tumor volumes were measured by digital caliper 3 times a week and body weights of all animals were recorded through the course of treatment (FIG. 4). Slight body weight loss was observed in the 100 mg/kg (4.5% body weight loss) treatment groups.

Anti-tumor activity was determined by assessing percentage of tumor volume in the treatment groups versus that in vehicle-treated (% T/C) or percentage of tumor regression compared to the starting volume (% regression). In vivo, treatment with Compound of formula (I) resulted in tumor regression in several human KRAS-mutant models including the NSCLC-derived Calu-6 (KRAS Q61K) and NCI-H358 (KRAS G12C) xenografts. In all cases, anti-tumor effects were dose-dependent. The Calu-6 model was sensitive to Compound of formula (I) with tumor regression observed at doses of 50 mg/kg and 100 mg/kg twice daily (BID) and 100 and 200 mg/kg once daily (QD) and 300 mg/kg once every other day (Q2D) in mice. Regression was also achieved in a second human NSCLC model, NCI-H358, at the 200 mg/kg QD dose. Furthermore, data from a dose fractionation efficacy study in Calu-6 xenografts demonstrated that across different dosing levels, Compound of formula (I) dosed QD and fractioned twice a day (BID) showed similar levels of anti-tumor activity. These results support exploration of QD or BID dose regimen in the clinic.

Collectively the in vitro and in vivo MAPK-pathway suppression and anti-proliferative activity observed for Compound of formula (I) at well-tolerated doses suggests that Compound of formula (I) may have anti-tumor activity in patients with tumors harboring activating lesions in the MAPK pathway and in particular may therefore be useful as a single agent or in combination with a second agent, such as an inhibitor affecting a different step of the MAPK pathway, for the treatment of NSCLC patients harboring KRAS mutations. Compound of formula (I) has been shown to have activity as a single agent against various other cancers that express gain-of-function mutations in the MAPK pathway, e.g., in RAS or RAF, including ovarian cancer, pancreatic cancer, and melanoma.

Example 2

Synergistic Effects of a Combination of Compound of Formula (I) and Trametinib on Cell Growth The effects of combining the Compound of formula (I) and the MEK1/2 inhibitor trametinib on the proliferation and signaling in NRAS mutant melanoma, KRAS mutant NSCLC, KRAS mutant PDAC and KRAS mutant CRC were tested as follows.

The CellTiter-Glo® (CTG) Luminescent Cell Viability Assay kit (Promega, Madison, Wis., USA) measures the amount of ATP present in a well after lysis of the cells. The ATP released upon lysis is measured in an enzymatic reaction which includes Luciferase and its substrate Luciferin. The amount of light emitted is proportional to the amount of ATP, which in turn is proportional to the number of live cells in the well. This assay is used to determine the proportion of viable cells after drug treatment.

NRAS mutant melanoma cell lines and KRAS mutant NSCLC cell lines were maintained in appropriate media.

| Cell Line | Mutation | Media* | Cancer Type |
|---|---|---|---|
| Calu-6 | $KRAS^{Q61K}$ | EMEM + 10% FBS | NSCLC |
| A549 | $KRAS^{G12S}$ | F12 + 10% FBS | NSCLC |
| HCC-2108 | $KRAS^{Q61H}$ | RPMI + 10% FBS | NSCLC |
| NCI-H2122 | $KRAS^{G12C}$ | RPMI + 10% FBS | NSCLC |
| NCI-H23 | $KRAS^{G12C}$ | RPMI + 10% FBS | NSCLC |
| NCI-H358 | $KRAS^{G12C}$ | RPMI + 10% FBS | NSCLC |
| NCI-H2030 | $KRAS^{G12C}$ | RPMI + 10% FBS | NSCLC |
| Hs 944.T | $NRAS^{Q61K}$ | RPMI + 10% FBS | Melanoma |
| IPC-298 | $NRAS^{Q61L}$ | RPMI + 10% FBS | Melanoma |
| MEL-JUSO | $NRAS^{Q61L}$ | RPMI + 10% FBS | Melanoma |
| MM127 | $NRAS^{G13R}$ | RPMI + 10% FBS | Melanoma |
| MM415 | $NRAS^{Q61L}$ | RPMI + 10% FBS | Melanoma |
| MM485 | $NRAS^{Q61R}$ | RPMI + 10% FBS | Melanoma |
| SK-MEL-2 | $NRAS^{Q61R}$ | EMEM + 10% FBS | Melanoma |

*RPMI: Roswell Park Memorial Institute medium.
FBS: Fetal Bovine Saline
EMEM: Eagle's minimum essential medium For NRAS mutant melanoma lines, combinations were assessed in a full grid matrix using Compound of formula (I) concentrations ranging from 0.002 to 10 μM and trametinib concentrations ranging from 1.52E-4 to 1 μM. For KRAS mutant NSCLC lines, combinations were assessed in a full grid or in a checkerboard formatted matrix using Compound of formula (I) concentrations ranging from 0.014 to 10 μM and trametinib concentrations ranging from 0.004 to 2.7 μM. Whether or not the combination was synergistic in a particular cell line was determined using synergy score (SS) and combination index (CI) at 50 percent inhibition ($CI_{50}$) effect sizes (Lehar et al., 2009). A summary of these values for each cell line is shown in the Table below.

TABLE

Summary of Compound of formula (I) × trametinib Synergy Scores and $CI_{50}$ values

| Cell Line | Cancer Type | KRAS Mutation | Loewe Synergy Score | Loewe Synergy Score Error | $CI_{50}$ | $CI_{50}$ Error | Synergy Determination |
|---|---|---|---|---|---|---|---|
| Hs 944.T | Melanoma | $NRAS^{Q61K}$ | 3.48 | 0.13 | 0.34 | 0.06 | Synergy |
| IPC-298 | Melanoma | $NRAS^{Q61L}$ | 4.22 | 0.20 | 0.40 | 0.16 | Synergy |
| MEL-JUSO | Melanoma | $NRAS^{Q61L}$ | 5.44 | 0.18 | 0.31 | 0.05 | Synergy |
| MM127 | Melanoma | $NRAS^{G13R}$ | 6.28 | 0.33 | 0.30 | 0.04 | Synergy |
| MM415 | Melanoma | $NRAS^{Q61L}$ | 2.69 | 0.11 | 0.29 | 0.04 | Synergy |
| MM485 | Melanoma | $NRAS^{Q61R}$ | 3.85 | 0.12 | 0.38 | 0.17 | Synergy |
| SK-MEL-2 | Melanoma | $NRAS^{Q61R}$ | 6.58 | 0.11 | 0.11 | 0.03 | Synergy |
| SK-MEL-30 | Melanoma | $NRAS^{Q61K}$ | 4.18 | 0.12 | 0.00 | 0.00 | Synergy |
| A549 | NSCLC | $KRAS^{G12S}$ | 5.65 | 0.26 | 0.42 | 0.06 | Synergy |
| Calu-6 | NSCLC | $KRAS^{Q61K}$ | 6.12 | 0.15 | 0.16 | 0.02 | Synergy |
| HCC-2108 | NSCLC | $KRAS^{Q61H}$ | 4.16 | 0.12 | 0.64 | 0.05 | Synergy |
| NCI-H2122 | NSCLC | $KRAS^{G12C}$ | 6.67 | 0.18 | 0.34 | 0.02 | Synergy |
| NCI-H23 | NSCLC | $KRAS^{G12C}$ | 2.59 | 0.12 | 0.41 | 0.11 | Synergy |
| NCI-H358 | NSCLC | $KRAS^{G12C}$ | 2.17 | 0.06 | 0.28 | 0.04 | Synergy |
| NCI- | NSCLC | $KRAS^{G12C}$ | 0.83 | 0.06 | 0.62 | 0.03 | No synergy/additivity |

@ Cell line likely not MAPK dependent as there was no effect on single agent treatment either.

The studies were repeated using KRAS-mutant PDAC and CRC models and the following results obtained.

TABLE

Summary of Compound of Formula I × trametinib Synergy Scores and CI$_{50}$ values in KRAS$^{mut}$ PDAC and CRC

| Cell Line | Cancer Type | KRAS Mutation | Loewe Synergy Score | Loewe Synergy Score Error | CI$_{50}$ | CI$_{50}$ Error | Synergy Determination |
|---|---|---|---|---|---|---|---|
| HCC-56 | CRC | KRAS$^{G12V}$ | 3.12 | 0.16 | 0.88 | 0.07 | Synergy |
| HCT 116 | CRC | KRAS$^{G13D}$ | 5.57 | 0.15 | 0.39 | 0.03 | Synergy |
| HCT-15 | CRC | KRAS$^{G13D}$ | 6.27 | 0.34 | 0.16 | 0.05 | Synergy |
| SK-CO-1 | CRC | KRAS$^{G12V}$ | 2.34 | 0.13 | 0.36 | 0.04 | Synergy |
| CFPAC-1 | PDAC | KRAS$^{G12V}$ | 3.65 | 0.23 | 0.09 | 0.02 | Synergy |
| HPAF-II | PDAC | KRAS$^{G12D}$ | 4.94 | 0.18 | 0.44 | 0.05 | Synergy |
| HUP-T4 | PDAC | KRAS$^{G12V}$ | 4.21 | 0.15 | 0.00 | 0.00 | Synergy |
| MIA PaCa-2 | PDAC | KRAS$^{G12C}$ | 3.65 | 0.06 | 0.46 | 0.02 | Synergy |
| PSN1 | PDAC | KRAS$^{G12R}$ | 7.51 | 0.07 | 0.27 | 0.01 | Synergy |
| QGP1 | PDAC | KRAS$^{G12V}$ | 1.55 | 0.07 | 0.42 | 0.03 | Additive/Synergy |
| SU.86.86 | PDAC | KRAS$^{G12D}$ | 3.44 | 0.21 | 0.55 | 0.05 | Synergy |
| TCC-PAN2 | PDAC | KRAS$^{G12R}$ | 3.34 | 0.12 | 0.00 | 0.00 | Synergy |

A general guideline for interpretation of the scores/values is provided in the Table below.

| Combination parameters | Effect description |
|---|---|
| SS > 3.0 and Best C.I. > 0.5 | Synergy |
| SS > 2.0 and Best C.I. < 0.5 | Synergy |
| SS > 2.0 and Best C.I. > 0.5 | Additive/Synergy |
| SS > 1.0 but < 2.0 and Best C.I. < 0.5 | Additive/Synergy |
| SS < 1.0 and Best C.I. < 0.5 | Additive |

As demonstrated from the Tables above, the Compound of formula (I) and trametinib have synergistic effects on cell growth in KRAS and NRAS mutant cell lines. Combining Compound of formula (I) and trametinib was moderately to strongly synergistic in all but one cell lines tested. In the one NSCLC cell line, NCI-H2030, in which no-synergy/additivity was observed, the lack of single agent response to either Compound of formula (I) or trametinib is very likely due to the fact that this model is not MAPK dependent.

Combining Compound of formula (I) and trametinib was moderately to strongly synergistic in all NRAS mutant melanoma cell. KRAS mutant PDAC, KRAS mutant CRC lines tested. Combining Compound of formula (I) and trametinib was moderately to strongly synergistic in 14 of 15 KRAS mutant NSCLC cell lines tested.

In the example of NCI-H2122, which showed the strongest synergy of the KRAS mutant NSCLC lines tested, the Loewe excess grid displays a difference of >40% between the Loewe dose additivity model and observed values at low doses of Compound of Formula (I) and Trametinib (0.041 to 0.37 µM Compound of Formula (I) and 0.11 µM Trametinib). In fact, single agent Compound of formula (I) has little to no activity at these low doses, with maximum inhibition values <30% below the 1 µM dose but the combination with trametinib at the same Compound of formula (I) doses has significant synergy (with Loewe excess >40%).

In SK-MEL-2, which had the strongest synergy of all NRAS melanoma cell lines tested, there is significant synergy at low doses of both trametinib and Compound of formula (I) (0.002 to 0.371 µM Compound of Formula (I) and 0.000152 to 0.001 µM of Trametinib). At the two lowest doses of trametinib (0.000152 - 0.000457 µM of Trametinib), there is strong synergy with Compound of formula (I) doses ranging from 0.014 to 0.124 µM, leading to anti-proliferative effects at concentrations where there is little to no single agent activity observed.

Compound of Formula (I) and Trametinib Inhibit Pharmacodynamic Biomarkers in KRAS and NRAS Mutant Cell Lines To probe the mechanism underlying the synergistic anti-proliferative effects of combining Compound of formula (I) and trametinib, the effects of this combination on MAPK signaling was investigated via western blot analysis. Cells were treated with single agent and combination doses of Compound of formula (I) (300 nM) and trametinib (3 nM) for 4 or 24 hours. As a further comparison to the combination doses, cells were also treated with 10-fold higher single agent doses of 3000 nM and 30 nM for Compound of formula (I) and trametinib, respectively.

In both NRAS mutant melanoma (IPC-298 and MM415) and KRAS mutant NSCLC (NCI-H23 and NCI-H358) cell lines examined, treatment of cells with the combination of Compound of formula (I) and trametinib was superior to either single agent alone at suppressing the pathway, as judged by the stronger suppression of pMEK1/2 and pERK1/2 levels in the combination compared to either single agent treatment. Moreover, suppression generated by the low dose combination was superior to what could be achieved at 10-fold higher levels of Compound of formula (I), and similar, albeit slightly less robust than was observed for at the higher trametinib levels. Thus, combined treatment of Compound of formula (I) and trametinib resulted in a highly synergistic suppression of MAPK signaling.

Example 3

In vivo Anti-Tumor Activity of Combination of Compound of Formula (I) with Trametinib.

As described below, the combined treatment with Compound of formula (I) and trametinib was found to lead to increased depth and durability of tumor response compared to either single agent in human KRAS mutant NSCLC, CRC, PDAC and NRAS mutant melanoma xenograft models. Therefore, the combination activity of Compound of Formula (I) and trametinib will likely achieve greater and more durable responses in patients whose cancers harbor an activated MAPK pathway.

Anti-Tumor Activitiy of a Combination of Compound of Formula (I) and a MEK Inhibitor in KRAS-Mutant NSCLC Cancer Models Anti-tumor activitiy of a combination of Compound of Formula (I) and a MEK inhibitor in KRAS-mutant NSCLC models Calu-6 NSCLC tumors were established in nude female mice. When tumors reached approximately 250 mm$^3$, mice were randomized according to tumor volume into treatment groups (n=7). Treatment was initiated on Day 10 post xenograft implant. Anti-tumor activity was determined on day 27 post tumor cell implantation; 17 days post initiation of treatment.

Figure 5:
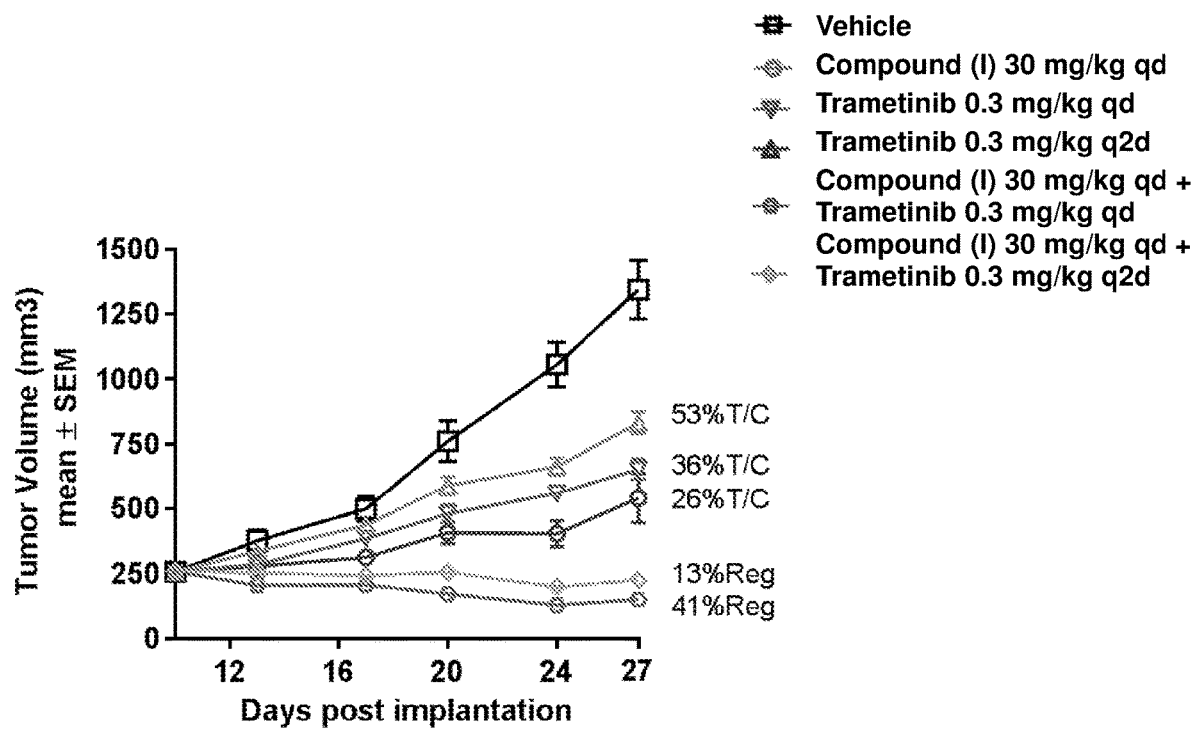
FIGS. 5 and 6 depict efficacy of Compound of formula (I) and MEK inhibitor trametinib used in combination in Calu-6 xenograft tumor models in mice. Animals with subcutaneous xenografts of Calu-6 received treatment with Compound of formula (I) and/or trametinib as indicated. Both depth (FIG. 5) and durability of response (FIG. 6) were demonstrated. Compounds were administered orally either daily (qd) or every other day (q2d) as indicated. Anti-tumor activity was determined by assessing percentage of tumor volume in the treatment groups versus that in vehicle-treated group (% T/C) or percentage of tumor regression compared to the starting volume (% regression, indicated as "% Reg" in FIGS. 2A-2B).
Figure 6:
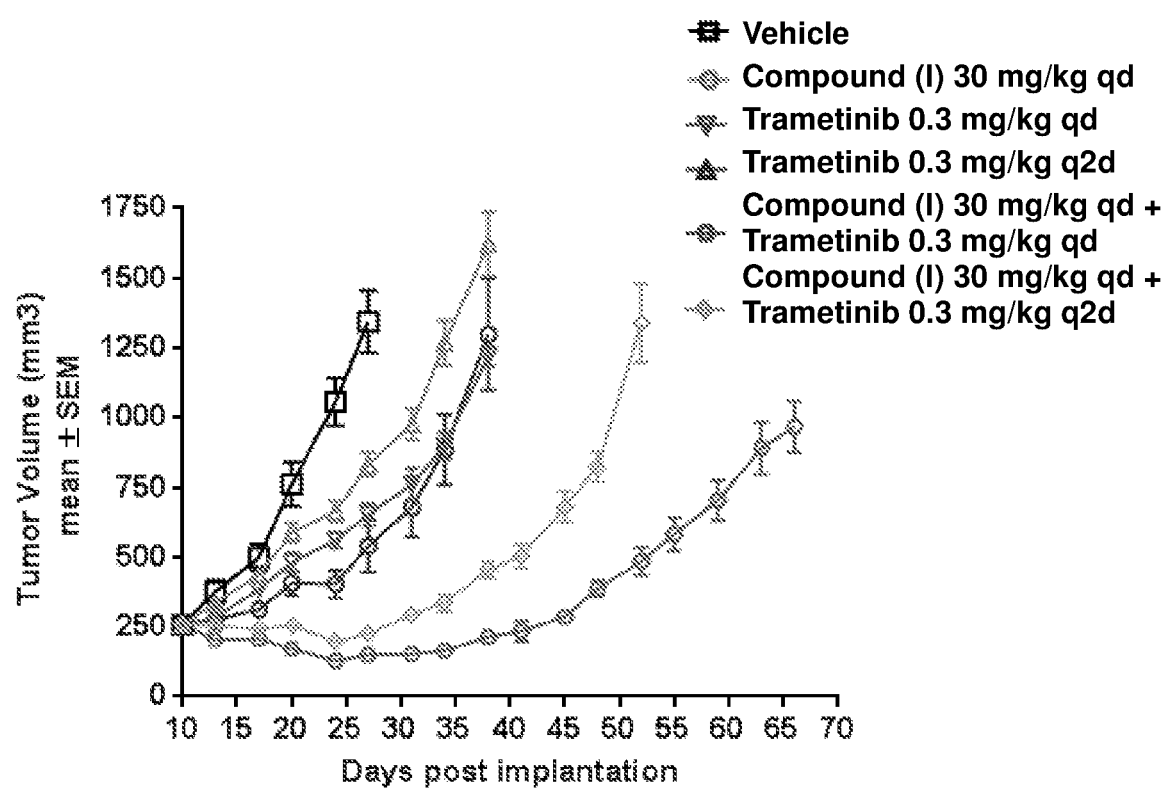

Test agents were administered orally once daily (qd) or once every other day (q2d) at the dose levels indicated in FIGS. 5 and 6 at a dosing volume of 10 ml/kg of animal body weight during course of treatment. Single agent was administered for 28 days, and the combination of Compound of formula (I) and trametinib was administered for 56 days. Tumor volumes were measured by digital caliper 2 times a week and body weights of all animals were recorded throughout the course of treatment.

Anti-tumor activity, mean change in tumor volume, mean percent change in body weight and survival 17 days post treatment initiation (27 days post implant) are reported in the Table below.

0.3 mg/kg q2d achieved 36% T/C and 53% T/C, respectively, 17 days post dosing. Combining Compound of formula (I) dosed at 30 mg/kg qd with trametinib dosed at either 0.3 mg/kg qd or 0.3 mg/kg q2d achieved 41% and 13 regressions, respectively, 17 days post dosing (FIG. 5).

To quantitatively assess the time to tumor progression amongst groups, the day that tumors surpassed an arbitrary cut-off of 700mm$^3$ in volume was noted. Again the combination of Compound of Formula (I) with either dose of trametinib achieved increased, statistically significant anti-tumor activity when compared to single agents. While tumors in mice dosed with Compound of formula (I) and trametinib as single agents progressed under treatment, the combination of Compound of formula (I) and trametinib together maintained tumor regressions for longer than monotherapy- with significant anti-tumor activity 28 days post dosing (38 days post tumor implantation) when compared to single agents.

All treatment groups were also well tolerated with minimal body weight loss for the duration of the study. In addition to the increased depth of response, the combination of Compound of formula (I) and trametinib also led to an increased durability of response (Table below and FIG. 6).

TABLE

Anti-tumor efficacy and tolerability of Compound of formula (I) and trametinib in the Calu-6 human NSCLC subcutaneous tumor xenograft model in mice on day 27 post-implantation

| Drug | Dose (mg/kg) and schedule | % T/C | % Tumor Regression | Change in tumor volume (mm3) Mean +/− SEM | Change in body weight (%) Mean +/− SEM | Survival (Survivors/ total mice) |
|---|---|---|---|---|---|---|
| Vehicle | — | | | 1086.91 ± 112.22 | 6.19 ± 0.93 | 7/7 |
| Compound of formula ((I) | 30 qd | 26* | | 282.92 ± 91.55 | −2.26 ± 0.89 | 7/7 |
| Trametinib | 0.3 qd | 36 | | 395.32 ± 36.43 | −1.55 ± 1.04 | 7/7 |
| Trametinib | 0.3 q2d | 53 | | 574.17 ± 30.67 | 1.71 ± 1.01 | 7/7 |
| Compound of formula (I) + Trametinib | 30 qd + 0.3 qd | | 41** | −107.68 ± 21.01 | −2.49 ± 1.60 | 7/7 |
| Compound of formula (I) + Trametinib | 30 qd + 0.3 q2d | | 13** | −33.86 ± 10.09 | −3.43 ± 0.93 | 7/7 |

Vehicle: Untreated
qd: once aday
q2d: every other day
The experiment was evaluated on study day 27.
*p = 0.0039 (Compound of formula (I) 30 mg/kg qd versus Vehicle treated group),
p < 0.0001 (Compound of formula (I) 30 mg/kg qd + trametinib 0.3 mg/kg qd, and Compound of formula (I) 30 mg/kg qd + trametinib 0.3 mg/kg q2d versus Vehicle treated group) (One-Way ANOVA Dunn's multiple comparison test).

Compound of formula (I) dosed at 30 mg/kg qd achieved 26% T/C, while trametinib dosed at either 0.3 mg/kg qd or

TABLE

Anti-tumor efficacy and tolerability of Compound of formula (I) and trametinib in the Calu-6 human NSCLC subcutaneous tumor xenograft model in mice on day 38 post-implantation

| Drug | Dose (mg/kg) and schedule | % T/C | % Tumor Regression | Change in tumor volume (mm3) Mean +/− SEM | Change in body weight (%) Mean +/− SEM | Survival (Survivors/ total) | Day to median tumor volume ~700 mm$^3$ |
|---|---|---|---|---|---|---|---|
| Vehicle | — | | — | — | — | | |
| Compound of formula (I) | 30 qd | 76 | — | 1040.54 ± 194.73 | 2.72 ± 0.66 | 7/7 | 31 |

TABLE-continued

Anti-tumor efficacy and tolerability of Compound of formula (I) and trametinib in the Calu-6 human NSCLC subcutaneous tumor xenograft model in mice on day 38 post-implantation

| Drug | Dose (mg/kg) and schedule | % T/C | % Tumor Regression | Change in tumor volume (mm3) Mean +/− SEM | Change in body weight (%) Mean +/− SEM | Survival (Survivors/total) | Day to median tumor volume ~700 mm³ |
|---|---|---|---|---|---|---|---|
| trametinib | 0.3 q2d | 100 | — | 1364.31 ± 107.51 | 2.75 ± 1.93 | 7/7 | 24 |
| trametinib | 0.3 qd | 70 | — | 961.52 ± 39.00 | 2.51 ± 1.48 | 7/7 | 27 |
| Compound of formula (I) + trametinib | 30 qd + 0.3 q2d | 14* | — | 195.78 ± 28.15 | 2.57 ± 2.88 | 7/7 | 45 |
| Compound of formula (I) + trametinib | 30 qd + 0.3 qd | | 17** | −44.63 ± 17.46 | 2.59 ± 1.50 | 7/7 | 59 |

Vehicle: Untreated
qd: once a day
q2d: every other day
% T/C was calculated using trametinib 0.3 mg/kg q2d group as a control
The experiment was evaluated on study day 38.
*p = 0.0041 (Compound of formula (I) 30 mg/kg qd + trametinib 0.3 mg/kg q2d versus trametinib 0.3 mg/kg q2d treated group),
**p < 0.0001 (Compound of formula (I) 30 mg/kg qd + trametinib 0.3 mg/kg qd versus trametinib 0.3 mg/kg q2d treated group) (One-Way ANOVA Dunn's multiple comparison test).

Anti-Tumor Activitiy of a Combination of Compound of Formula (I) and a MEK Inhibitor in KRAS-Mutant Colorectal Cancer Models HCT116 (KRAS G13D) colorectal cancer (CRC) tumors were established in nude female mice. When tumors reached approximately 230 mm³, mice were randomized according to tumor volume into treatment groups (n=6). Treatment was initiated on Day 14 post xenograft implant. Anti-tumor activity was determined on day 31 post tumor cell implantation (the last day of vehicle treated mice).

Test agents were administered orally once daily (qd) or once every other day (q2d) at the dose levels indicated in FIG. 16 (A) at a dosing volume of 10 ml/kg of animal body weight during course of treatment. Tumor volumes were measured by digital caliper 2 times a week and body weights of all animals were recorded throughout the course of treatment. Compound of formula (I) dosed at 100 mg/kg qd achieved 30% T/C, while trametinib dosed at 0.3 mg/kg qd achieved 44% T/C, 17 days post dosing. Combining Compound of formula (I) dosed at 100 mg/kg qd with trametinib dosed at 0.3 mg/kg q2d achieved 26% regression, 17 days post dosing (FIG. 16). On day 24 post tumor implantation, one mouse was sacrificed due to increased body weight loss. On day 31, the last day of vehicle treatment, mice treated with Compound of formula (I) had a combined body weight loss of 4%; mice treated with trametinib exhibited 3.5% body weight loss, and mice treated with the combination of Compound of formula (I) and trametinib showed 9% body weight loss .

Anti-Tumor Activitiy of a Combination of Compound of Formula (I) and a MEK Inhibitor in PDAC Cancer Models Patient derived 2043 PDAC (KRAS$^{G12D}$) tumors were established in nude female mice. When tumors reached approximately 230 mm³, mice were randomized according to tumor volume into treatment groups (n=6). Treatment was initiated on Day 52 post xenograft implant. Anti-tumor activity was determined on day 73 post tumor cell implantation.

Test agents were administered orally once daily (qd) or once every other day (q2d) at the dose levels indicated in FIG. 17 A at a dosing volume of 10 ml/kg of animal body weight during course of treatment. Tumor volumes were measured by digital caliper 2 times a week and body weights of all animals were recorded throughout the course of treatment. Compound of formula (I) dosed at 100 mg/kg qd achieved 55% T/C, while trametinib dosed at 0.3 mg/kg qd achieved 32% T/C, 21 days post dosing. Combining Compound of formula (I) dosed at 100 mg/kg qd with trametinib dosed at 0.3 mg/kg q2d achieved 35 regression, 21 days post dosing (FIG. 17). On day 66 post tumor implantation, one mouse was sacrificed due to increased body weight loss. On day 73, the last day of combination treatment, mice treated with compound of formula I had a combined body weight loss of 0.6%; mice treated with tramentinib exhibited 0.3% body weight gain, and mice treated with the combination of compound of formula I and trametinib showed 9.6% body weight loss.

Anti-tumor activitiy of a combination of Compound of Formula (I) and a MEK inhibitor in melanoma cancer models The anti-tumor activity of the combination of Compound of Formula (I) and a MEK inhibitor in several human NRAS mutant melanoma xenografts was studied as follows.

(i) SKMEL30 melanoma models

SKMEL30 (NRAS$^{Q61K}$) melanoma tumors were established in nude female mice. Treatments were administered at a dose volume of 10 mL/kg. Mice were randomized into treatment groups (n=9) on day 12 following tumor implantation, when the average tumor volume was 190 mm3. Anti-tumor activity was determined on day 34 post tumor cell implantation; 22 days post initiation of treatment Test agents were administered orally once (qd) or twice daily (bid) at the dose levels indicated in FIG. 18 at a dosing volume of 10 ml/kg of animal body weight during course of treatment. Tumor volumes were measured by digital caliper 2 times a week and body weights of all animals were recorded throughout the course of treatment. On day 34, the last day that the vehicle treated group was on study, Compound of formula (I) treatment resulted in 5% tumor regression, while 0 .3 mg/kg qd of Trametinib resulted in8%T/C. The combination of Compound of formula (I) with trametinib at 0.15 mg/kg qd led to a further increased anti-tumor activity of 48% tumor regression when compared to the vehicle treated group (FIG. 18). All treatment groups were well tolerated with minimal body weight loss for the duration of the study. Single agent groups were dosed continuously for the duration of the study; in the Compound of formula I and Trametinib combination group, a brief dosing holiday of Trametinib only (day 28 till day 31) was provided after which the full combination was resumed to the end of the study (ii) NRAS-mutant melanoma model 20667

Patient derived "20667" (NRAS$^{Q61R}$) melanoma tumors were established in nude female mice. When tumors reached approximately 300 mm$^3$, mice were randomized according to tumor volume into treatment groups (n=7). Treatment was initiated on Day 17 post xenograft implant. Anti-tumor activity of the single agents was determined on day 34 post tumor implantation, while the anti-tumor activity of the combination between Compound of formula (I) and trametinib was determined on day 48 post tumor cell implantation.

Test agents were administered orally once daily (qd) or twice daily (bid) at the dose levels indicated in FIG. 19 at a dosing volume of 10 ml/kg of animal body weight during course of treatment. Tumor volumes were measured by digital caliper 2 times a week and body weights of all animals were recorded throughout the course of treatment. Compound of formula (I) dosed at 100 mg/kg qd achieved 87% T/C, while trametinib dosed at 0.3 mg/kg qd achieved 82% T/C, 17 days post dosing. Combining Compound of formula (I) dosed at 50 mg/kg bid with trametinib dosed at 0.3 mg/kg qd achieved 68% regression, 31 days post dosing (FIG. 19). All treatment groups were well tolerated with minimal body weight loss for the duration of the study.

(iii) NRAS-mutant melanoma model 21124

Patient derived "21124" (NRAS$^{Q61H}$) melanoma tumors were established in nude female mice. When tumors reached approximately 300 mm$^3$, mice were randomized according to tumor volume into treatment groups (n=5). Treatment was initiated on Day 45 post xenograft implant. Anti-tumor activity was determined on day 66 post tumor cell implantation.

Test agents were administered orally once daily (qd) or twice daily (bid) at the dose levels indicated in FIG. 20 at a dosing volume of 10 ml/kg of animal body weight during course of treatment. Tumor volumes were measured by digital caliper 2 times a week and body weights of all animals were recorded throughout the course of treatment. Compound of formula (I) dosed at 100 mg/kg qd achieved 10% T/C, while trametinib dosed at 0.3 mg/kg qd achieved 54% T/C, 17 days post dosing. Combining Compound of formula (I) dosed at 50 mg/kg bid with trametinib dosed at 0.0375 mg/kg qd achieved 40% regression, 21 days post dosing (FIG. 20). All treatment groups were well tolerated with no body weight loss for the duration of the study.)

(iv) NRAS-mutant melanoma model "20864"

Patient derived "21124" (NRAS$^{Q61H}$) melanoma tumors were established in nude female mice. When tumors reached approximately 300 mm$^3$, mice were randomized according to tumor volume into treatment groups (n=5). Treatment was initiated on Day 19 post xenograft implant. Anti-tumor activity of the single agents was determined on day 33 post tumor implantation, while the anti-tumor activity of the combination between Compound of formula (I) and trametinib was determined on day 55 post tumor cell implantation.

Test agents were administered orally once daily (qd) or twice daily (bid) at the dose levels indicated in FIG. 21 at a dosing volume of 10 ml/kg of animal body weight during course of treatment. Tumor volumes were measured by digital caliper 2 times a week and body weights of all animals were recorded throughout the course of treatment. Compound of formula (I) dosed at 50 mg/kg bid achieved 30% T/C, while trametinib dosed at 0.3 mg/kg qd achieved 84% T/C, 14 days post dosing. Combining Compound of formula (I) dosed at 50 mg/kg bid with trametinib dosed at 0.0375 mg/kg qd achieved 12% regression, 36 days post dosing (FIG. 21). On day 33, 2 mice in the combination group were sacrificed for pharmcodynamic studies, and the efficacy was carried with n=3 for the remainder of the study. All treatment groups were well tolerated with minimal body weight loss for the duration of the study.

Collectively, the data suggest that combined treatment with Compound of formula (I) and trametinib may achieve greater and more durable responses in patients with activated MAPK pathway due to gain-of-function mutations in the MAPK pathway. Some of the combination doses tested showed slight body weight loss (up to 10%,) however, the majority of combination doses tested. were well tolerated as judged by minimal body weight loss Example 3

A Phase I Study of Compound of Formula (I) alone and in Combination with Trametinib in Adult Patients with Advanced Solid Tumors Harboring MAPK Pathway Alterations The recommended starting dose and regimen of Compound of formula (I) as single agent in this study is 100 mg once a day (QD) orally based on the preclinical safety, tolerability data, pharmacokinetic (PK) and/or pharmacodynamic (PD) data in preclinical studies, as well as exploratory human efficacious dose range projection in order to minimize exposure to potentially toxic drug levels while limiting the number of patients that might receive inactive doses.

Starting doses of 100 mg, 200 mg, 250 mg, 300 mg, or 400 mg are envisioned; preliminary data suggesting a starting dose of 250 mg once daily (QD) may be effective on solid tumors. For maximum flexibility of dosing, Compound of formula (I) may be prepared as 50 mg and/or 100 mg tablets for oral administration. The QD regimen has been demonstrated to be efficacious and tolerated in preclinical studies. In Calu6 xenografts, similar levels of efficacy were achieved with either QD or fractionated twice a day (BID) regimens, suggesting efficacy is related to overall exposure. The predicted human PK and the predicted half-life (~9h), also suggest efficacious exposure can be achieved with QD dosing.

The dose escalation of Compound of formula (I) in combination with a MEK inhibitor, e.g., trametinib, will begin with a dosing regimen identified for Compound of formula (I) as a single agent: the starting dose of Compound of formula (I) may be lower than the single agent dose. The selection of this dose thus should minimize exposure to potentially toxic drug levels while limiting the number of patients that might receive doses too low to provide good efficacy. MEK inhibitor, e.g., trametinib will be administered at a flat dose of 2 mg which is the single agent recommended dosage.

In the dose expansion part, patients in the combination arm will be treated at the recommended dose and regimen for the drug combination based on the dose escalation data.

In the combination studies, a daily dose of 400 mg of Compound of formula (I) QD and a daily dose of 1 mg of trametinib or a daily dose of 400 mg of Compound of formula (I) and a daily dose of 2 mg trametinib are envisaged. The daily dose of Compound of formula (I) may be preferentially administered twice daily, whilst the daily dose of trametinib administered once daily. Other doses such as in the Table below may also be administered.

TABLE

Dose levels of the combination of Compound
of formula (I) and trametinib

| Daily dose for Compound of formula (I)* | Daily dose for trametinib* |
|---|---|
| 100 mg | 0.5 mg, 1.0 mg, 1.5 mg or 2.0 mg |
| 200 mg | 0.5 mg, 1.0 mg, 1.5 mg or 2.0 mg |
| 400 mg | 0.5 mg, 1.0 mg, 1.5 mg or 2.0 mg |
| 800 mg | 0.5 mg, 1.0 mg, 1.5 mg or 2.0 mg |
| 1200 mg | 0.5 mg, 1.0 mg, 1.5 mg or 2.0 mg |

*Daily doses of either Compound of formula (I) or trametinib, or both, may be administered once or twice daily.

In addition, an efficacious dosage can be determined by monitoring biomarkers indicative of MAP kinase pathway inhibition. In particular, DUSP6 (dual specificity phosphatase 6) is a known biomarker for this pathway, and in vivo levels of DUSP6 have been shown to drop in a subject receiving a dosage of Compound of formula (I) that is associated with efficacious plasma levels of Compound of formula (I). Thus, DUSP6 may be used as a pharmacodynamics biomarker in subjects treated with Compound of formula (I), whether as a single agent or in combination with a MEK inhibitor.

Example 4

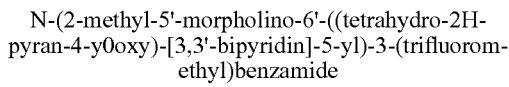

Compound of formula (II) is a morpholine-substituted biaryl compound of the following structure Compound (II)

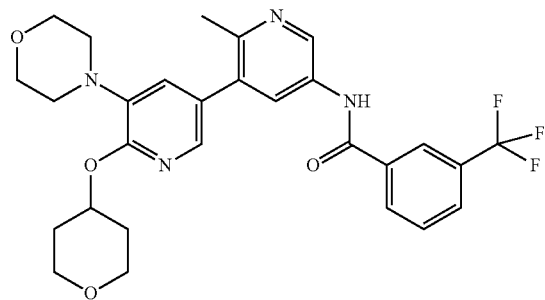

Compound of formula (II) is an inhibitor of B-Raf and C-Raf. The compound is disclosed and its preparation described in example 131 in published PCT patent application WO2014/151616.

Example 4A

Compound of formula (II) is a type II inhibitor of both mutated and wild-type B-Raf and C-Raf.

TABLE 5

Half maximal inhibitory concentration (IC-50) of Compound
of formula (II) on B-Raf, B-Raf V600E and C-Raf

| Target | Kinase activity inhibition IC$_{50}$ [mM] | % of target binding at 1 mM |
|---|---|---|
| BRAF | 0.0015 | 99.7 |
| BRAF$^{V600E}$ | 0.001 | 99.9 |
| CRAF | 0.0004 | 99.8 |

Example 4B

Compound of formula (II) exhibits activity on numerous human cancer cell lines that express mutations in the MAPK pathway as shown in the following Table. Activity is especially strong on cell lines that harbor at least one mutation in BRAF or RAS.

TABLE 6

Effect of Compound of formula (II) on proliferation
in a panel of human cancer cell lines.

| Cell line | Dabrafenib IC$_{50}$ [mM] | Compound of formula (II) IC$_{50}$ [mM] | B-Raf/Ras alteration |
|---|---|---|---|
| A375 | 0.003 | 0.13 | BRaf Mutant |
| IPC-298 | 0.27 | 0.07 | NRas Mutant |
| Calu-6 | 23 | 1.4 | KRas Mutant |
| HCT116 | 17 | 0.98 | KRas Mutant |

Different tumor cell lines were treated with dose titrations of Compound of formula (II) for 5 days, and cell proliferation was determined using the CellTiter-Glo ™ luminescent cell viability assay.

Example 4C

Figure 7:
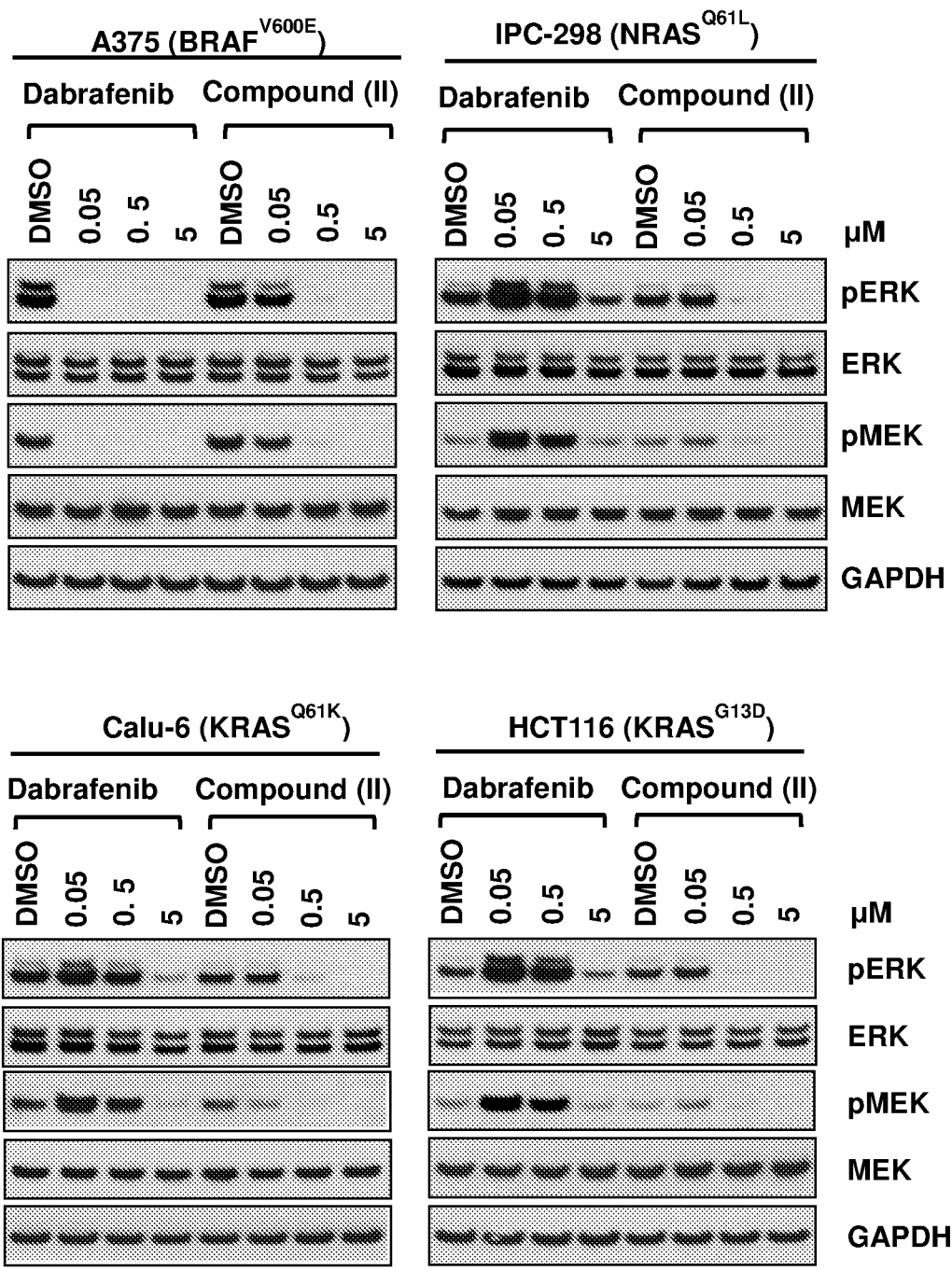
FIG. 7. Cell lines harboring different BRAF or RAS mutations were treated with DMSO, dabrafenib or Compound of formula (II) at the indicated concentrations for 2 hr. Inhibition of MEK or ERK phosphorylation was measured by western blot analysis. Compound of formula (II) inhibits oncogenic signaling and proliferation in tumor cells with BRAF, NRAS or KRAS mutations with minimal paradoxical activation.

The activity of Compound of formula (II) and dabrafenib in cell lines harboring BRAFV600, NRAS or KRAS mutations was compared (FIG. 7). In A375 cells, both dabrafenib and Compound of formula (II) inhibited MEK and ERK phosphorylation to near completion at 0.05 and 0.5 µM, respectively. In contrast, in the three cell lines harboring either a NRAS or KRAS mutation, dabrafenib treatment at 0.05 and 0.5 p,M led to an increase in MEK and ERK phosphorylation, and only at 5 µM showed modest inhibition. In comparison, Compound of formula (II) showed dose-dependent inhibition of MEK and ERK phosphorylation without apparent pathway activation in all three RAS mutant models (minimal activation of pMEK in IPC-298 and HCT116) (FIG. 7). The ability of Compound of formula (II) to inhibit pathway signaling was comparable in cells harboring different RAS mutations and those with the BRAF V600 mutation, reaching near complete inhibition of pMEK and pERK at 0.5 µM.

Figure 8:
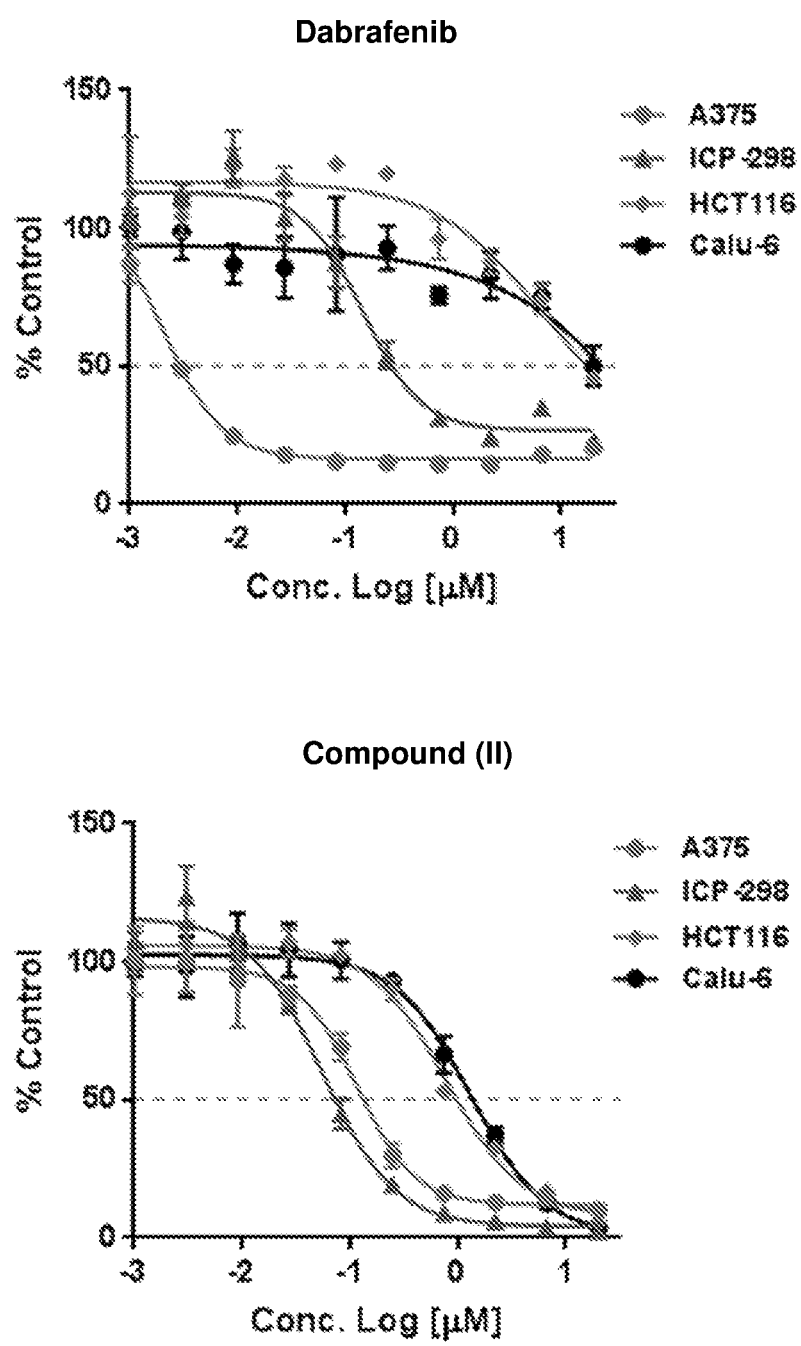
FIG. 8. Growth inhibition of cell lines after 5 days of treatment with dabrafenib (upper panel) or Compound of formula (II) (lower panel) was determined.

The anti-proliferation activity of Compound of formula (II) and dabrafenib in these cell lines was also investigated (FIG. 8). Consistent with the signaling data, dabrafenib showed the most potent anti-proliferative activity in BRAF$^{V600}$E A375 cells (IC$_{50}$=0.003 µM), approximately 100× less potent in NRAS$^{mut}$ IPC-298 cells (IC$_{50}$=0.27 µM), and very little activity in the two KRAS$^{mut}$ cell lines (Calu-6 IC$_{50}$=23 µM, HCT116 IC$_{50}$=17 µM). In contrast, Compound of formula (II) showed less IC$_{50}$ dose shift in RAS$^{mut}$ models compared to the BRAF$^{mut}$ model and exhibited dose-dependent growth inhibition in all cell lines examined, with IC$_{50}$ values of 0.13 µM, 0.07 µM, 1.4 µM, and 0.98 µM in A375, IPC-298, Calu-6 and HCT116, respectively.

A similar experiment with the Compound of Formula (I) also demonstrated that the Compound of Formula (I) produced similar results (see Table below).

| | BRAFV600E monomer pERK IC50 [µM] | Wild type (WT) RAF dimer 2nd site monomer pERK IC50 [µM] | Dimer/ Monomer inhibition ratio |
|---|---|---|---|
| Dabrafenib | 0.005 | 3 | 600 |
| Compound of formula (I) | 0.059 | 0.078 | 1.3 |

Figure 9:
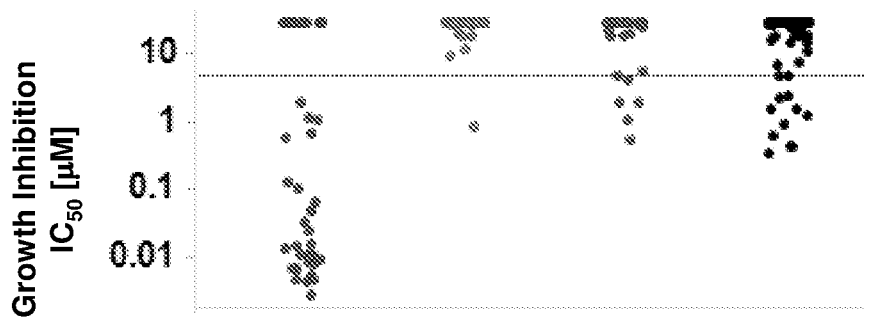
FIG. 9. Dot plots of $IC_{50}$ values for growth inhibition in 357 human cancer cell lines by Compound of formula (II) or dabrafenib following 3 days of inhibitor treatment. The dotted line represents an $IC_{50}$ of 5µM which was used as a cut-off for cell line sensitivity to the inhibitors. The number of sensitive and resistant cell lines to each inhibitor among BRAF mutant, KRAS mutant, NRAS mutant, or wild-type (WT) cells is indicated below the graph. A Fisher's Exact Test was performed to determine the statistical significance of inhibitor activity in BRAF or RAS mutant cell lines vs WT cell lines.
Figure 9:
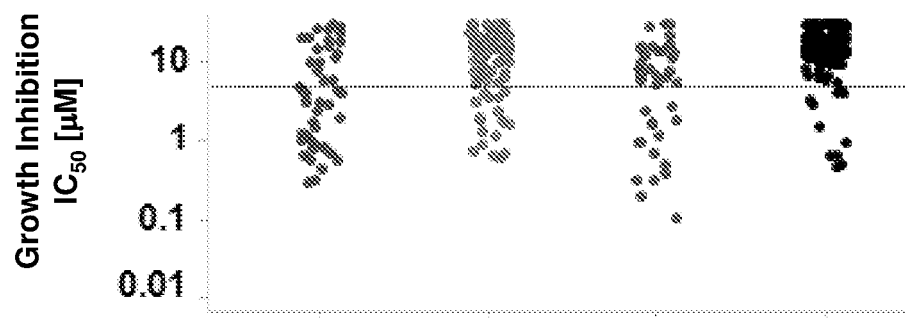

These data demonstrate that Compound of formula (I) and Compound of formula (II) exhibit a mode of inhibition distinct from the class of RAF monomer inhibitors. Their activity inhibiting both RAF monomers and dimers suggest it should be effective in treating tumors harboring BRAF or RAS mutations, in contrast to dabrafenib which is unlikely to be effective in RAS-mutant tumors Example 4D Antiproliferative activity of Compound of formula (II) was analyzed in a broad panel of genetically characterized human cancer cell line models. Activity of Compound of formula (II) was compared with that of dabrafenib in 357 cell lines with mutations in BRAF, KRAS, or NRAS, or wild-type for both BRAF and RAS (FIG. 9). Each data point represents the inhibitor IC50 value in a cell line following 3 days of treatment. Using an inhibitor IC50 of 5 µM as a cut-off, the number of sensitive (IC50<5 µM) and insensitive (IC50>5 µM) lines was indicated within each genetic group for Compound of formula (II) and dabrafenib. For example, Compound of formula (II) shows anti-proliferative activity in cancer cell lines that harbor non-V600 mutation with or without a co-occurring KRAS mutation, including ovarian cancer cell line Hey-A8 (KRAS$^{G120D}$/BRAF$^{G464E}$, IC$_{50}$=0.63 µM), breast cancer cell line MDA-MB-231 (KRAS$^{G13D}$/BRAF$^{G464V}$, IC$_{50}$=3.4 µM), and lung cancer cell line NCI-H1666 (BRAF$^{G466V}$, IC$_{50}$=3.97 µM). In comparison, the BRAF monomer inhibitor dabrafenib had IC$_{50}$>30 µM in all three cell line models. Data were analyzed with a Fisher's exact test to evaluate whether sensitivity of cell lines to the inhibitor treatment was significantly increased in the mutant group when compared to wild-type cell lines. For Compound of formula (II), cell lines harboring B-Raf, KRAS, or N-Ras mutations exhibited significantly increased sensitivity as compared to those that are wild-type, with p-values of $3.09 \times 10^{-17}$, $1.19 \times 10^{-4}$, and $1.26 \times 10^{-6}$, respectively. The odds ratios are 28.9, 4.6 and 10.6, respectively. In comparison, higher sensitivity to dabrafenib was only significant in cell lines harboring B-Raf mutations, but not with KRAS or N-Ras mutations, with p-values of $1.9 \times 10^{-15}$, 0.11, and 0.25 respectively.

Example 5

Anti-Tumor Activity of Compound of Formula (II) in KRAS-Mutant NSCLC Models

Figure 10:
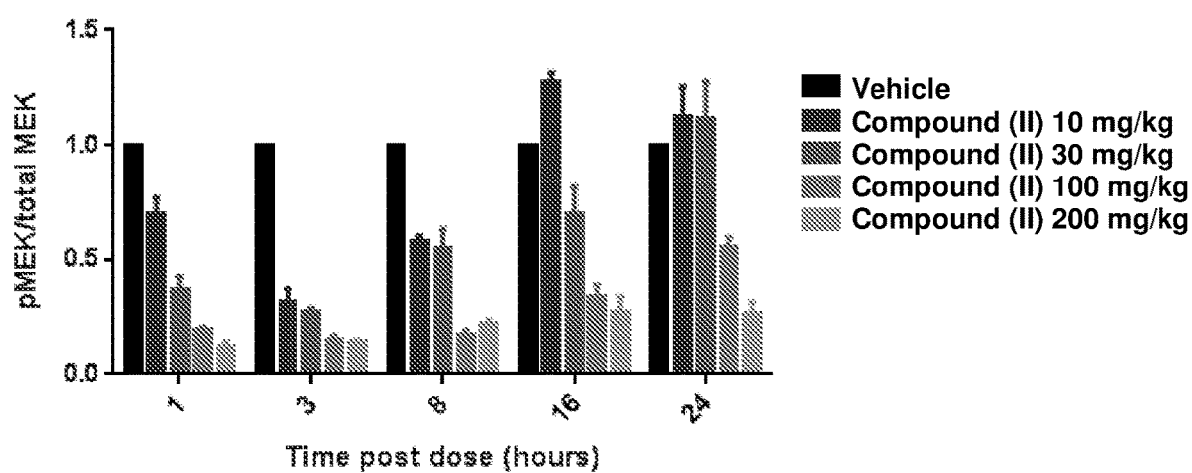
FIG. 10. Tumor samples were collected at the indicated time points following a single dose of vehicle or increasing doses of Compound of formula (II) in the Calu-6 tumor-bearing animals to determine phosphorylated MEK (pMEK) levels. pMEK levels are represented as the ratio of pMEK/total MEK in the treatment group compared to vehicle control at each time point.
Figure 11:
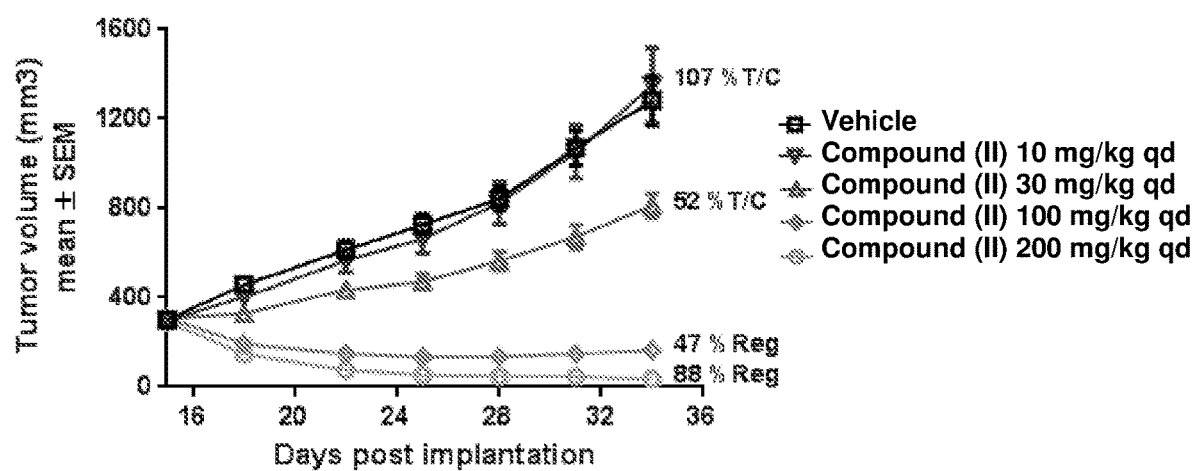
FIG. 11. Calu-6 tumor xenograft growth inhibition was measured following treatment with vehicle or Compound of formula (II) across four dose levels. Tumor volume is represented as the mean tumor volume from 6 animals per treatment group±standard error of the mean (SEM). Animals with subcutaneous xenografts of Calu-6 received treatment with Compound of formula (II) as indicated. Compound of formula (II) was administered daily (qd). Anti-tumor activity was determined by assessing percentage of tumor volume in the treatment groups versus that in the vehicle-treated group (% T/C) or percentage of tumor regression compared to the starting volume (% regression, indicated as "% Reg" in FIG. 11).

Both signaling inhibition and anti-tumor efficacy of Compound of formula (II) were investigated in the KRAS mutant Calu-6 model in vivo. Calu-6 tumor xenografts were generated by implanting cells in 50% Matrigel™ subcutaneously into the right flank of female nude mice (6-8 weeks old). Tumor-bearing mice were randomized into treatment groups and treated with a single oral dose of Compound of formula (II) across a wide dose range (from 10 to 200 mg/kg). Tumor tissues were then collected at multiple time points post-dose to levels of phospho- and total MEK1/2 using the MesoScale Discovery (MSD) platform or DUSP6 mRNA by quantitative PCR (qPCR). As shown in FIG. 10, treatment with Compound of formula (II) led to inhibition of MEK phosphorylation in a dose-dependent manner both in degree and in duration. Compound of formula (II) at both 100 and 200 mg/kg was able to suppress phosphorylated MEK (pMEK) to greater than 50% for more than 16 hours. Subsequently, anti-tumor efficacy of Compound of formula (II) was evaluated in the same tumor xenograft model (FIG. 11). Tumor bearing animals were dosed with vehicle, Compound of formula (II) at 10, 30, 100, or 200 mg/kg, administered orally every day (qd) for 19 days. Anti-tumor activity was determined by assessing percentage of tumor volume in the treatment groups versus that in vehicle-treated (% T/C) or percentage of tumor regression compared to the starting volume (% regression). Tumor volume and body weights were collected at the time of randomization and twice per week for the study duration. Tumor volume was determined by measurement with calipers and calculated using a modified ellipsoid formula, where tumor volume (TV) (mm$^3$)= $[((1 \times w2) \times 3.14159))/6]$, where 1 is the longest axis of the tumor and w is perpendicular to 1. In line with pMEK inhibition, treatment with Compound of formula (II) resulted in dose dependent anti-tumor activity starting from 30 mg/kg (FIG. 11). Treatment with 30 mg/kg of Compound of formula (II) led to a 52% T/C, while treatment at 100 and 200 mg/kg resulted in tumor regressions of 47% and 88%, respectively, in line with the more durable pathway inhibition at the two higher dose levels.

Figure 12:
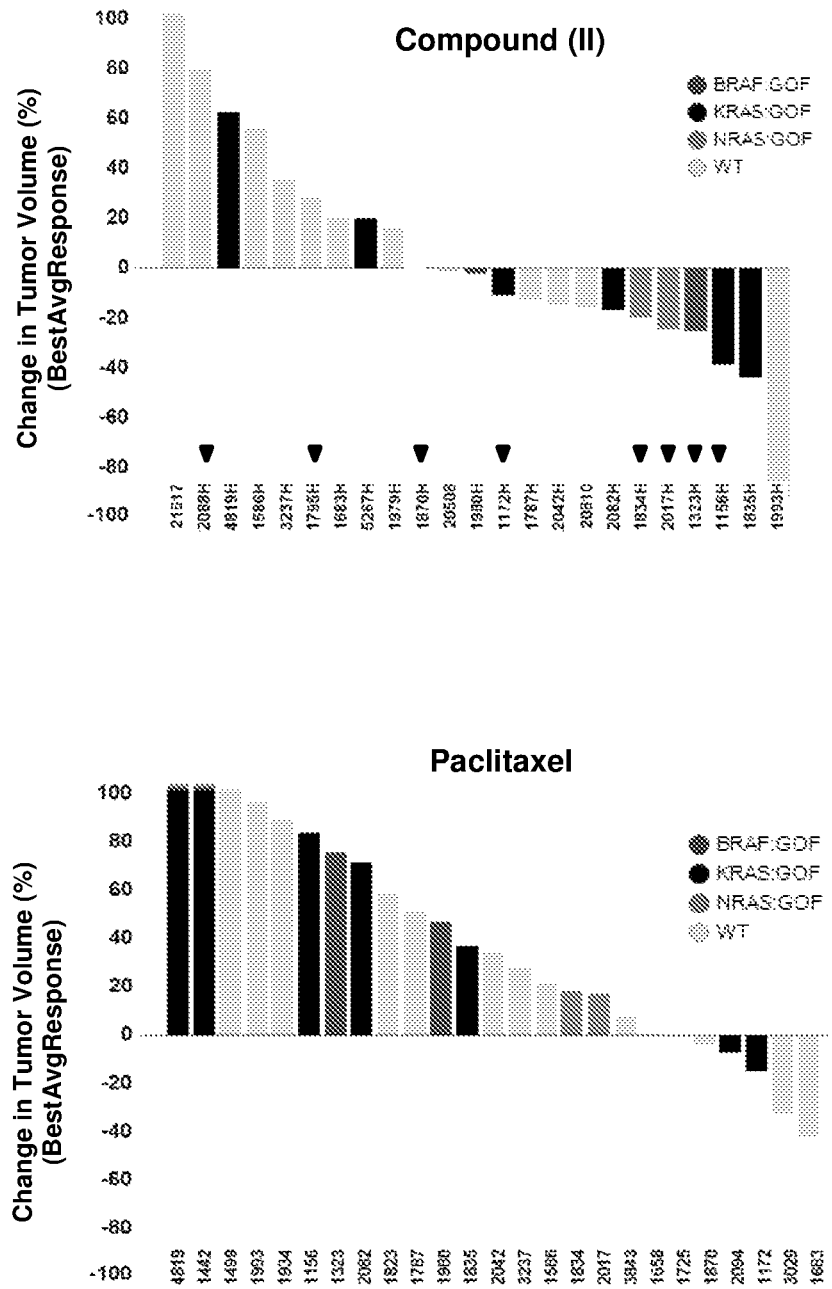
FIG. 12. In vivo antitumor activity of Compound of formula (II) was assessed in a panel of 23 NSCLC patient derived xenograft (PDX) models, presented as the % of change in tumor volume at the time of measurement compared to initial tumor volume, positive values indicated tumor growth and negative values indicated tumor regression. Compound of formula (II) was dosed orally once daily at 60 mg/kg or 200 mg/kg (indicated by ▼). Each tumor is annotated for BRAF or RAS mutation status. Tumor response to paclitaxel in a panel of NSCLC PDX models was included for comparison. GOF=gain-of-function, WT=wildtype.

To assess the antitumor activity of Compound of formula (II) further, a large scale in vivo screen of Compound of formula (II) efficacy in 23 patient derived xenograft (PDX) models derived from patient with non-small cell lung cancer (NSCLC) was performed (FIG. 12). Tumor response is presented as a waterfall plot of best average percentage change in tumor volume with Compound of formula (II) treatment, and tumors were annotated for their mutation status of RAS or BRAF. Compound of formula (II) dosed at 60 mg/kg or 200 mg/kg (▼) daily led to tumor growth inhibition in a subset of NSCLC PDX tumors, in which tumors that harbor mutation of B-Raf, N-Ras, or KRAS, were enriched among the better responders. One of the B-Raf mutant tumors, HLUX1323, harbors a D594N mutation which has been shown to activate signaling mediated through Raf dimerization and Compound of formula (II) led to 26% of tumor shrinkage in this model. These data further support the anticancer efficacy of Compound of formula (II) in both Ras and B-Raf mutant cancer cells as a result of its selective activity in inhibiting Raf monomers or dimers and the oncogenic MEK/ERK signaling.

Example 6

Synergistic Effect of Compound of Formula (II) with a MEK Inhibitor

Figure 13:
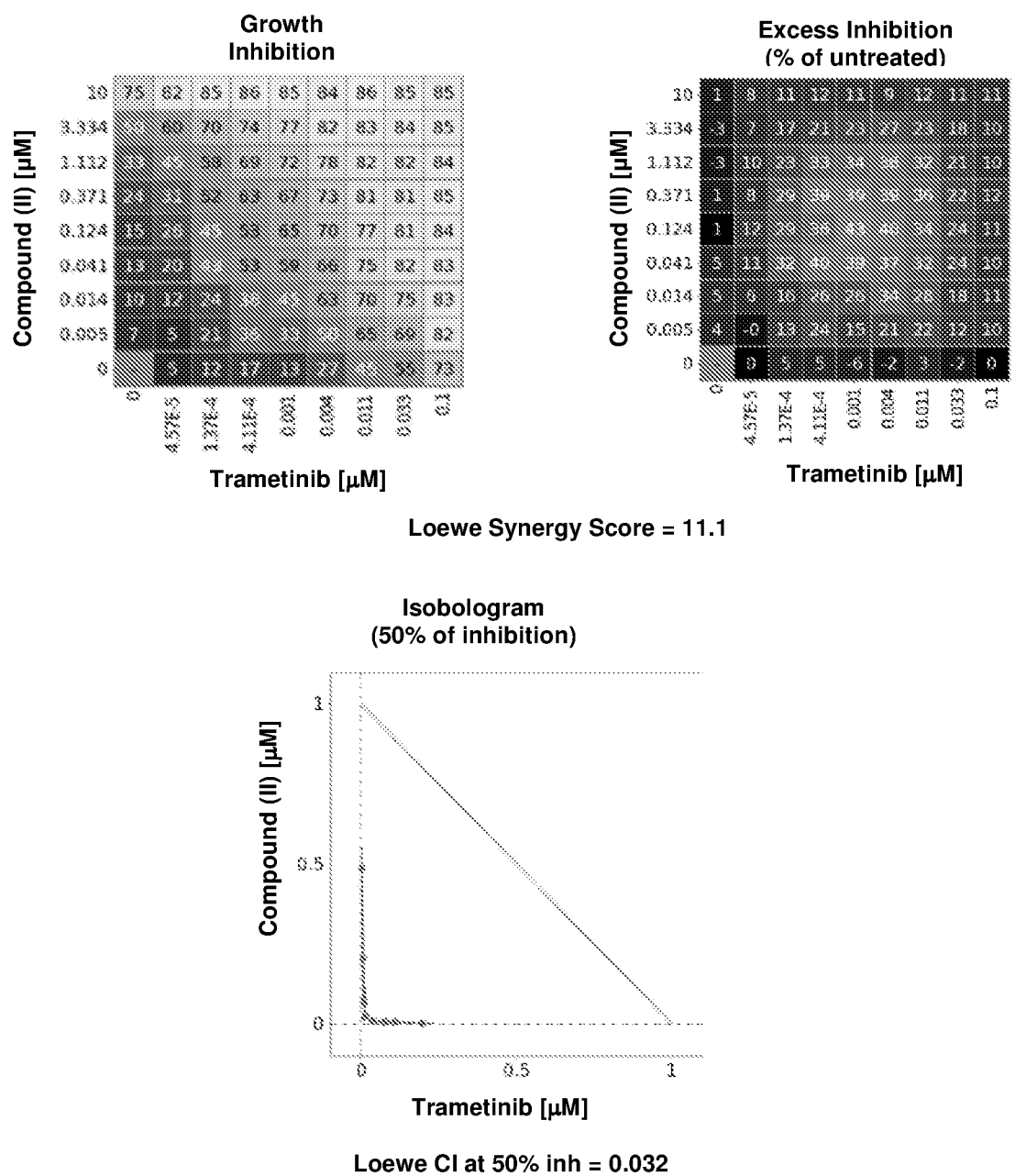
FIG. 13. Anti-proliferative combination activity of Compound of formula (II) and trametinib in HPAF-II (KRAS (G12D mutant) pancreas derived cells was assessed. Top left panel: dose matrix representing percentages of growth inhibition relative to DMSO by Compound of formula (II), trametinib, and the combination following 5 days of treatment. Top right panel: excess inhibition values representing the deviation between the combination effect and the calculated additivity effect of the two single agents using the Loewe model. The calculated Loewe synergy score is indicated. Lower panel: isobologram analysis of the dose matrix data, the dark grey line represents the data points and the light grey line indicates additivity. The calculated Loewe Combination Index (CI) at 50% growth inhibition is indicated.

Growth inhibition of HPAF-II cells (KRAS mutant) was measured following treatment with Compound of formula (II) or trametinib as single agent, or with the two in combination, across a wide dose range. Isobolograms and synergy scores were generated to assess the combination activity. As shown in FIG. 13, Compound of formula (II) in combination with trametinib had a synergistic effect on inhibiting HPAF-II cell growth, with a Loewe synergy score of 11.1.

Figure 14:
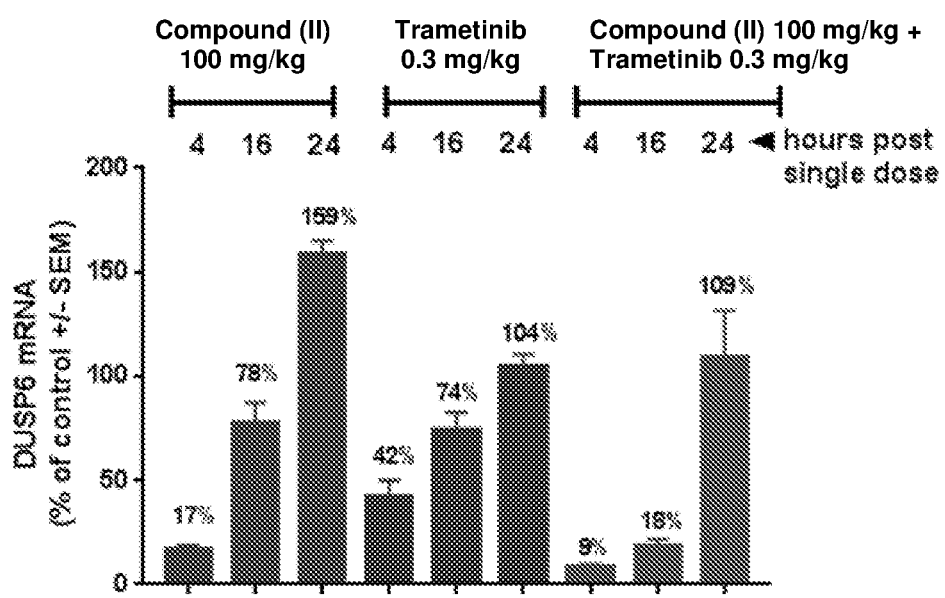
FIG. 14. In vivo activity of Compound of formula (II) and trametinib as single agents or in combination in the HPAF-II xenograft model. Signaling inhibition following a single dose of the treatment as measured by DUSP6 (dual specificity phosphatase 6) mRNA levels. In addition, an efficacious dosage can be determined by monitoring biomarkers indicative of MAP kinase pathway inhibition. In particular, DUSP6 is a known biomarker for this pathway, and in vivo levels of DUSP6 have been shown to drop in response to Compound of formula (II) that is associated with efficacious plasma levels of Compound of formula (II).

To evaluate the effect of the combination treatment on signaling inhibition versus either agent alone, nude mice bearing HPAF-II xenograft tumors were treated with a single dose of Compound of formula (II) at 100 mg/kg, trametinib at 0.3 mg/kg or the two inhibitors combined. DUSP6 mRNA levels, as a measurement of pathway activity, was determined in tumor samples collected at multiple time points post-dose. As shown in FIG. 14, Compound of formula (II) treatment led to 83% inhibition of DUSP6 at 4 hours (hrs) post dose compared to vehicle control, however, this inhibition was not durable as demonstrated by the increased levels of DUSP6 at 16 and 24 hrs post dose. Similarly, trametinib treatment led to a partial and transient inhibition of DUSP6. In contrast, the combination of Compound of formula (II) and trametinib led to a more sustained DUSP6 inhibition, showing greater than 80% of inhibition even at 16 hours post dose. Anti-tumor efficacy of the different treatments in the same tumor xenograft model was evaluated: Tumor-bearing animals were dosed with vehicle, Compound of formula (II) at 100 mg/kg qd, trametinib at 0.3 mg/kg qd, or a combination of both for 10 days (FIG. 15). In line with DUSP6 inhibition, the combination of Compound of formula (II) and trametinib treatment resulted in greater anti-tumor activity than either of the single agents alone, resulting in 33% regression as compared to 40% T/C or 54% T/C by Compound of formula (II) or trametinib, respectively (FIG. 15). Collectively, these data suggest that combined treatment with Compound of formula (II) and trametinib achieves greater and more durable responses in patients with activated MAPK pathway due to gain-of-function mutations in the MAPK pathway. It is also expected that Compound of formula (I) in combination with trametinib achieves greater and more durable responses than either treatment alone, resulting in enhanced anti-tumor activity in patients with activated MAPK pathway due to gain-of-function mutations in the MAPK pathway.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A pharmaceutical combination comprising a Raf inhibitor which is the Compound of formula (I)

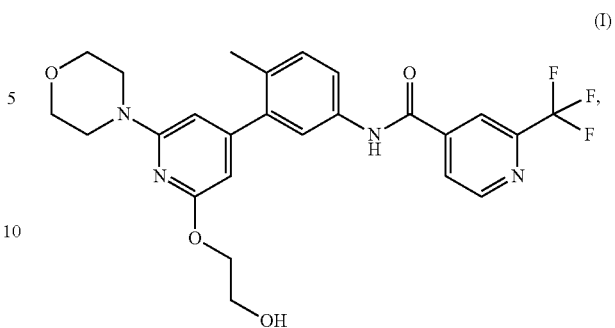

or a pharmaceutically acceptable salt thereof,
and (b) a MEK inhibitor, wherein the MEK inhibitor is trametinib, or a pharmaceutically acceptable salt or solvate thereof.

2. The pharmaceutical combination according to claim 1 wherein trametinib is in the form of a dimethyl sulfoxide solvate.

3. A method of treating cancer by treating a patient in need thereof with a pharmaceutical combination comprising a compound of formula (I)

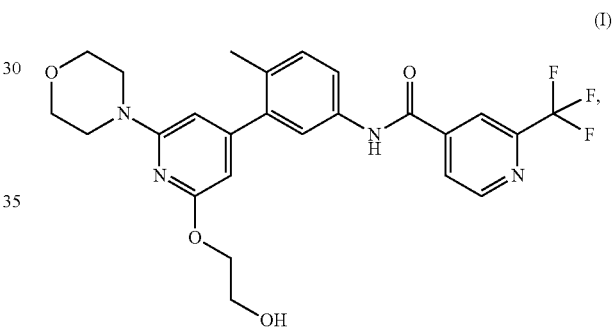

or a pharmaceutically acceptable salt thereof, and trametinib, or a pharmaceutically acceptable salt or solvate thereof, wherein the cancer is selected from the group consisting of KRAS-mutant NSCLC (non-small cell lung cancer), NRAS-mutant melanoma, KRAS-mutant ovarian cancer and KRAS-mutant pancreatic cancer.

4. The method according to claim 3 wherein the cancer is N-RAS mutant melanoma.

5. The method according to claim 3 wherein the cancer is NSCLC.

6. The method according to claim 5 wherein the NSCLC is KRAS-mutant NSCLC, BRAF-mutant NSCLC, or both KRAS-mutant and BRAF-mutant NSCLC.

7. The method according to claim 5 wherein the NSCLC is characterized by a BRAF V600E mutation or a BRAF non-V600E mutation.

8. The method according to claim 3, wherein the cancer is advanced or metastatic cancer.

9. The method according to claim 3 wherein the cancer is a BRAF V600-mutant melanoma or BRAF V600-mutant NSCLC, wherein the melanoma is responding to treatment or is no longer responding to treatment with a BRAF inhibitor, or a MEK inhibitor or both a BRAF and MEK inhibitor; wherein the BRAF inhibitor is selected from dabrafenib and vemurafenib; and the MEK inhibitor is selected from trametinib and cobimetinib.

10. The method according to claim 9 wherein the cancer is BRAF V600-mutant melanoma which is resistant to treatment with a combination of dabrafenib and trametinib or to treatment with a combination of vemurafenib and cobimetinib.

11. The method according to claim 9 wherein the cancer is BRAF V600-mutant NSCLC which is resistant to treatment with a combination of dabrafenib and trametinib.

12. The method according to claim 3 wherein the cancer has progressed following standard of care or for whom no effective standard therapy exists; wherein the cancer is selected from NSCLC and melanoma.

13. The method of claim 3 wherein the KRAS-mutant pancreatic cancer is KRAS-mutant pancreatic ductal adenocarcinoma (PDAC)).

* * * * *